US011453919B2

(12) United States Patent
Eaton et al.

(10) Patent No.: US 11,453,919 B2
(45) Date of Patent: Sep. 27, 2022

(54) COMPOSITIONS AND METHODS FOR DETECTING GROUP B *STREPTOCOCCUS* NUCLEIC ACID

(71) Applicant: GEN-PROBE INCORPORATED, San Diego, CA (US)

(72) Inventors: Barbara L. Eaton, San Diego, CA (US); Benjamin Grobarczyk, Saive (BE); Yves Ozog, Zonhoven (BE); Renaud Close, Villers-le-Bouillet (BE); Laurent Franzil, Flémalle (BE)

(73) Assignee: Gen-Probe Incorporated, San Diego, CA (US)

( * ) Notice: Subject to any disclaimer, the term of this patent is extended or adjusted under 35 U.S.C. 154(b) by 308 days.

(21) Appl. No.: 16/537,421

(22) Filed: Aug. 9, 2019

(65) Prior Publication Data
US 2020/0140928 A1 May 7, 2020

Related U.S. Application Data

(60) Provisional application No. 62/684,317, filed on Jun. 13, 2018.

(51) Int. Cl.
| C12Q 1/689 | (2018.01) |
| C12Q 1/686 | (2018.01) |
| G01N 21/64 | (2006.01) |
| G01N 21/76 | (2006.01) |

(52) U.S. Cl.
CPC ............ *C12Q 1/689* (2013.01); *C12Q 1/686* (2013.01); *G01N 21/6428* (2013.01); *G01N 21/76* (2013.01); *C12Q 2600/158* (2013.01); *G01N 2021/6432* (2013.01); *G01N 2021/6439* (2013.01)

(58) Field of Classification Search
CPC .. C12Q 1/686; C12Q 1/689; C12Q 2600/158; C12Q 2600/16; G01N 2021/6432
See application file for complete search history.

(56) References Cited

U.S. PATENT DOCUMENTS

| 8,067,207 | B2 | 11/2011 | Bergeron et al. |
| 9,562,262 | B2 | 2/2017 | Peytavi et al. |
| 2004/0009482 | A1 | 1/2004 | Dattagupta et al. |
| 2004/0253617 | A1 | 12/2004 | Fanrong et al. |
| 2006/0088849 | A1 | 4/2006 | Happe |
| 2006/0252064 | A1* | 11/2006 | Wu ........................ C12Q 1/689 435/6.11 |
| 2010/0028884 | A1 | 2/2010 | Gygax et al. |
| 2015/0086987 | A1 | 3/2015 | Wolff et al. |
| 2017/0349937 | A1 | 12/2017 | Savelkoul |

FOREIGN PATENT DOCUMENTS

| CN | 1712546 A | 12/2008 |
| CN | 104730128 B | 4/2017 |
| CN | 107541509 A | 1/2018 |
| WO | WO 03068813 | * 8/2003 |
| WO | WO 2003/080870 A1 | 10/2003 |
| WO | WO 2019/239394 A1 | 12/2019 |

OTHER PUBLICATIONS

Ye et al., BMC Bioinformatics, 13 (134) 1-11, (Year: 2012).*
GenBank: HQ148671.1, https://www.ncbi.nlm.nih.gov/nuccore/HQ148671.1, pp. 1-2, September (Year: 2013).*
Bergh, et al., "Detection of group B *Streptococci* (GBS) in vaginal swabs using real-time PCR with TaqMan probe hybridization," Indian J. Med Res, 119 (Suppl), pp. 221-223, (May 2004).
Berry, et al., "Comparison of the Panther Fusion and BD MAX Group B *Streptococcus* (GBS) Assays for Detection of GBS in Prenatal Screening Specimens," Journal of Clinical Microbiology, vol. 57, Issue 11, e01034-19, (Nov. 2019).
Boving, et al., "Eight-Plex PCR and Liquid-Array Detection of Bacterial and Viral Pathogens in Cerebrospinal Fluid from Patients with Suspected Meningitis," Journal of Clinical Microbiology, vol. 27, No. 4, p. 908-913, (Apr. 2009).
PCT/IB2019/056814 International Search Report and Written Opinion dated Oct. 21, 2019.
Shin, et al., "Comparison of Three Nucleic Acid Amplification Tests and Culture for Detection of Group B *Streptococcus* from Enrichment Broth," Journal of Clinical Microbiology, vol. 57, Issue 6, e01958-18, (Jun. 2019).
U.S. Appl. No. 62/684,317, filed Jun. 13, 2018, Expired.
PCT/IB2019/056814, filed Jul. 11, 2013, WO 2019/239394, Published.
Bergseng, et al., "Real-time PCR targeting the sip gene for detection of group B *Streptococcus* colonization in pregnant women at delivery," Journal of Medical Microbiology, 56, 223-228, (2007).
Golden, et al., "Evaluation of a real-time fluorescent PCR assay for rapid detection of Group B *Streptococci* in neonatal blood," Diagnostic Microbiology and Infectious Disease, 50, 7-13, (2004).
Hazzani, et al., "Epidemiological characterization of serotype group B *Streptococci* neonatal infections associated with interleukin-6 level s a sensitive parameter for the early diagnosis," Saudi Journal of Biological Sciences, 25, 1356-1364, (2018).
Ke, et al., "Development of Conventional and Real-Time PCR Assays for the Rapid Detection of Group B *Streptococci*," Clinical Chemistry, 46:3, 324-331, (2000).
McKenna, et al., "Loop-mediated isothermal amplification assay for rapid detection of *Streptococcus agalactiae* (group B *Streptococcus*) in vaginal swabs—a proof of concept study," Journal of Medical Microbiology, 66:297-300. (2017).

(Continued)

*Primary Examiner* — Cynthia B Wilder
(74) *Attorney, Agent, or Firm* — Jeffrey E. Landes; Alston & Bird LLP

(57) ABSTRACT

Disclosed are nucleic acid oligomers, including amplification oligomers and detection probes, for detection of Group B *Streptococcus* (GBS; *Streptococcus agalactiae*) nucleic acid. Also disclosed are methods of specific nucleic acid amplification and detection using the disclosed oligomers, as well as corresponding reaction mixtures and kits.

8 Claims, No Drawings

Specification includes a Sequence Listing.

(56) References Cited

OTHER PUBLICATIONS

GB2104178.5 Combined Search and Examination Report dated Nov. 23, 2021.
GB2104180.1 Combined Search and Examination Report dated Nov. 23, 2021.
GB2104181.9 Combined Search and Examination Report dated Nov. 19, 2021.
GB2104185.0 Combined Search and Examination Report dated Nov. 19, 2021.
GB2104190.0 Combined Search and Examination Report dated Nov. 19, 2021.
GB2100233.2 Examination Report dated Nov. 30, 2021.

* cited by examiner

COMPOSITIONS AND METHODS FOR DETECTING GROUP B *STREPTOCOCCUS* NUCLEIC ACID

CROSS REFERENCE TO RELATED APPLICATIONS

This application claims the benefit under 35 USC 119(e) of U.S. Provisional Application No. 62/684,317 filed Jun. 13, 2018, which is hereby incorporated by reference in its entirety for all purposes.

REFERENCE TO SEQUENCE LISTING

This application includes an electronic sequence listing in a file named "535511_SEQLIST.TXT," created on Aug. 9, 2019 and containing 8,299 bytes, which is hereby incorporated by reference in its entirety for all purposes.

BACKGROUND OF THE INVENTION

Group B *Streptococcus* (GBS), or *Streptococcus agalactiae*, is a gram-positive bacterium associated with transient colonization of mucosal membranes throughout the body, including the vagina, gastrointestinal tract, and urethra. GBS rarely causes disease in healthy individuals but can cause serious illness in immune compromised patients, elderly individuals, and newborn infants. Of particular concern is neonatal infection caused by vertical transmission during labor and birthing. Transmission from an asymptomatically colonized mother to the neonate can result in early-onset invasive GBS disease, which is the leading cause of sepsis and meningitis in newborns in the United States. Early-onset invasive GBS disease in newborns can result in death or long-term disabilities such as mental retardation and hearing or vision loss. Buchan et al., *J. Clin. Microbiol.* 53:443-448, 2015.

The identification of GBS during routine screening results in administration of intra partum prophylaxis to mitigate transmission of bacteria and reduce the chance of invasive disease. The implementation of this screening and prophylaxis strategy has reduced the incidence of early-onset GBS by 60 to 86%. Lin et al., *Am. J. Obstet. Gynecol.* 184:1204-1210, 2001. Since 2010, CDC guidelines have included molecular diagnostic testing as an option in parallel with or in addition to culture. Current tests include the Cepheid GBS LB and BD max GBS tests, which target the CFB gene.

There is a need in the art for GBS assays having improved sensitivity and/or the potential to protect against isolate variance of a single gene, including, for example, assays that can detect GBS serotypes Ia, Ib, Ic, II, III, IV, V, VI, VII, VIII and IX, including non-hemolytic isolate.

SUMMARY OF THE INVENTION

In one aspect, the present invention provides a composition for determining the presence or absence of Group B *Streptococcus* (GBS) in a sample. In some embodiments, the composition includes at least one of a first amplification oligomer combination and a second amplification oligomer combination, where
(I) the first amplification oligomer combination includes first and second SIP-specific amplification oligomers capable of amplifying a target region of a GBS SIP target nucleic acid, where the first and second SIP-specific amplification oligomers comprise, respectively, first (A) and second (B) SIP-specific target-hybridizing sequences selected from
  (a) (A) SEQ ID NO:3, or an RNA equivalent or DNA/RNA chimeric thereof, and
   (B) SEQ ID NO:4, or an RNA equivalent or DNA/RNA chimeric thereof; and
  (b) (A) SEQ ID NO:7, or an RNA equivalent or DNA/RNA chimeric thereof, and
   (B) SEQ ID NO:8, or an RNA equivalent or DNA/RNA chimeric thereof;
and
(II) the second amplification oligomer combination includes first and second CFB-specific amplification oligomers capable of amplifying a target region of a GBS CFB target nucleic acid, where the first and second CFB-specific amplification oligomers comprise, respectively, first (A') and second (B') CFB-specific target-hybridizing sequences selected from
  (a) (A') a sequence that is from about 17 to about 24 contiguous nucleotides contained in the sequence of SEQ ID NO:26, or an RNA equivalent or DNA/RNA chimeric thereof, and
   (B') SEQ ID NO:13 or SEQ ID NO:15, or an RNA equivalent or DNA/RNA chimeric thereof;
  (b) (A') SEQ ID NO:16, or an RNA equivalent or DNA/RNA chimeric thereof, and
   (B') SEQ ID NO:17, or an RNA equivalent or DNA/RNA chimeric thereof;
  (c) (A') SEQ ID NO:18, or an RNA equivalent or DNA/RNA chimeric thereof, and
   (B') SEQ ID NO:15, or an RNA equivalent or DNA/RNA chimeric thereof; and
  (d) (A') SEQ ID NO:20, or an RNA equivalent or DNA/RNA chimeric thereof, and
   (B') SEQ ID NO:21, or an RNA equivalent or DNA/RNA chimeric thereof.

In some embodiments of a composition as above where the composition includes the first amplification oligomer combination, the composition further includes a SIP-specific detection probe oligomer comprising a SIP-specific detection probe target-hybridizing sequence that is from about 15 to about 35 nucleotides in length and is configured to hybridize to a target sequence contained within a SIP amplicon amplifiable by the first and second SIP-specific amplification oligomers. In some such embodiments, the first and second SIP-specific target-hybridizing sequences are the target-hybridizing sequences of (I)(a) and the SIP-specific detection probe target-hybridizing sequence is SEQ ID NO:9, or an RNA equivalent or DNA/RNA chimeric thereof. In other embodiments, the first and second SIP-specific target-hybridizing sequences are the target-hybridizing sequences of (I)(b) and the SIP-specific detection probe target-hybridizing sequence is SEQ ID NO:11, or an RNA equivalent or DNA/RNA chimeric thereof. In some variations, the SIP-specific detection probe oligomer further includes a detectable label such as, for example, a fluorescent or chemiluminescent label. In some embodiments comprising a detectably labeled probe oligomer, the detectable label is a fluorescent label and the SIP-specific detection probe oligomer further includes a non-fluorescent quencher.

In some embodiments of a composition as above where the CFB-specific target-hybridizing sequences are the target-hybridizing sequences of (II)(a), the first CFB-specific target-hybridizing sequence of (II)(a) includes at least the sequence of SEQ ID NO:28, or an RNA equivalent or DNA/RNA chimeric thereof. In some such embodiments, the first CFB-specific target-hybridizing sequence of (II)(a)

is contained in the sequence of SEQ ID NO:27, or an RNA equivalent or DNA/RNA chimeric thereof; in some such variations, the first CFB-specific target-hybridizing sequence of (II)(a) is SEQ ID NO:12 or SEQ ID NO:14, or an RNA equivalent or DNA/RNA chimeric thereof. In other embodiments where the CFB-specific target-hybridizing sequences are the target-hybridizing sequences of (II)(a), the first CFB-specific target-hybridizing sequence of (II)(a) is SEQ ID NO:18, or an RNA equivalent or DNA/RNA chimeric thereof. Particularly suitable first (A') and second (B') CFB-specific target-hybridizing sequences of (II)(a) include (i) (A') SEQ ID NO:12, or an RNA equivalent or DNA/RNA chimeric thereof, and
      (B') SEQ ID NO:13, or an RNA equivalent or DNA/RNA chimeric thereof;
   (ii) (A') SEQ ID NO:12, or an RNA equivalent or DNA/RNA chimeric thereof, and
      (B') SEQ ID NO:15, or an RNA equivalent or DNA/RNA chimeric thereof;
   (iii) (A') SEQ ID NO:14, or an RNA equivalent or DNA/RNA chimeric thereof, and
      (B') SEQ ID NO:15, or an RNA equivalent or DNA/RNA chimeric thereof; and
   (iv) (A') SEQ ID NO:18, or an RNA equivalent or DNA/RNA chimeric thereof, and
      (B') SEQ ID NO:15, or an RNA equivalent or DNA/RNA chimeric thereof.

In some embodiments of a composition as above where the composition includes the first amplification oligomer combination, the composition further comprises a CFB-specific detection probe oligomer comprising a CFB-specific detection probe target-hybridizing sequence that is from about 15 to about 35 nucleotides in length and is configured to hybridize to a target sequence contained within a CFB amplicon amplifiable by the first and second CFB-specific amplification oligomers. In some such embodiments, the first and second CFB-specific target-hybridizing sequences are the target-hybridizing sequences of (II)(b) and the CFB-specific detection probe target-hybridizing sequence is SEQ ID NO:24, or an RNA equivalent or DNA/RNA chimeric thereof; the first and second CFB-specific target-hybridizing sequences are the target-hybridizing sequences of (II)(d) and the CFB-specific detection probe target-hybridizing sequence is SEQ ID NO:25, or an RNA equivalent or DNA/RNA chimeric thereof; the first and second CFB-specific target-hybridizing sequences are the target-hybridizing sequences of (II)(a) and the CFB-specific detection probe target-hybridizing sequence is SEQ ID NO:22 or SEQ ID NO:23, or an RNA equivalent or DNA/RNA chimeric thereof; or the first and second CFB-specific target-hybridizing sequences are the target-hybridizing sequences of (II)(c) and the CFB-specific detection probe target-hybridizing sequence is SEQ ID NO:23, or an RNA equivalent or DNA/RNA chimeric thereof. In some variations, the CFB-specific detection probe oligomer further includes a detectable label such as, for example, a fluorescent or chemiluminescent label. In some embodiments comprising a detectably labeled probe oligomer, the detectable label is a fluorescent label and the CFB-specific detection probe oligomer further includes a non-fluorescent quencher.

In certain embodiments of a composition for determining the presence or absence of GBS in a sample as above, the composition includes both the first and second amplification oligomer combinations.

In another aspect, the present invention provides a composition for determining the presence or absence of GBS in a sample, where the composition includes an amplification oligomer combination comprising first and second SIP-specific amplification oligomers capable of amplifying a target region of a GBS SIP target nucleic acid. Particularly suitable first and second SIP-specific amplification oligomers comprise, respectively, first (A) and second (B) SIP-specific target-hybridizing sequences selected from (a) (A) SEQ ID NO:3, or an RNA equivalent or DNA/RNA chimeric thereof, and
      (B) SEQ ID NO:4, or an RNA equivalent or DNA/RNA chimeric thereof and
   (b) (A) SEQ ID NO:7, or an RNA equivalent or DNA/RNA chimeric thereof, and
      (B) SEQ ID NO:8, or an RNA equivalent or DNA/RNA chimeric thereof.

In some variations, the composition further includes a SIP-specific detection probe oligomer comprising a SIP-specific detection probe target-hybridizing sequence that is from about 15 to about 35 nucleotides in length and is configured to hybridize to a target sequence contained within a SIP amplicon amplifiable by the first and second SIP-specific amplification oligomers. In some such embodiments, the first and second SIP-specific target-hybridizing sequences are the target-hybridizing sequences of (a) and the SIP-specific detection probe target-hybridizing sequence is SEQ ID NO:9, or an RNA equivalent or DNA/RNA chimeric thereof. In other embodiments, the first and second SIP-specific target-hybridizing sequences are the target-hybridizing sequences of (b) and the SIP-specific detection probe target-hybridizing sequence is SEQ ID NO:11, or an RNA equivalent or DNA/RNA chimeric thereof. In some variations, the SIP-specific detection probe oligomer further includes a detectable label such as, for example, a fluorescent or chemiluminescent label. In some embodiments comprising a detectably labeled probe oligomer, the detectable label is a fluorescent label and the SIP-specific detection probe oligomer further includes a non-fluorescent quencher. In some variations of a composition as above, the composition further includes a second amplification oligomer combination capable of amplifying a target region of a GBS CFB target nucleic acid.

In another aspect, the present invention provides a composition for determining the presence or absence of GBS in a sample, where the composition includes an amplification oligomer combination comprising first and second CFB-specific amplification oligomers capable of amplifying a target region of a GBS CFB target nucleic acid. Particularly suitable first and second CFB-specific amplification oligomers comprise, respectively, first (A) and second (B) CFB-specific target-hybridizing sequences selected from (a) (A) a sequence that is from about 17 to about 24 contiguous nucleotides contained in the sequence of SEQ ID NO:26, or an RNA equivalent or DNA/RNA chimeric thereof, and
      (B) SEQ ID NO:13 or SEQ ID NO:15, or an RNA equivalent or DNA/RNA chimeric thereof;
   (b) (A) SEQ ID NO:16, or an RNA equivalent or DNA/RNA chimeric thereof, and
      (B) SEQ ID NO:17, or an RNA equivalent or DNA/RNA chimeric thereof;

(c) (A) SEQ ID NO:18, or an RNA equivalent or DNA/RNA chimeric thereof, and
(B) SEQ ID NO:15, or an RNA equivalent or DNA/RNA chimeric thereof; and
(d) (A) SEQ ID NO:20, or an RNA equivalent or DNA/RNA chimeric thereof, and
(B) SEQ ID NO:21, or an RNA equivalent or DNA/RNA chimeric thereof.

In certain embodiments, the first CFB-specific target-hybridizing sequence of (a) includes at least the sequence of SEQ ID NO:28, or an RNA equivalent or DNA/RNA chimeric thereof. In some such embodiments, the first CFB-specific target-hybridizing sequence of (a) is contained in the sequence of SEQ ID NO:27, or an RNA equivalent or DNA/RNA chimeric thereof, in some such variations, the first CFB-specific target-hybridizing sequence of (a) is SEQ ID NO:12 or SEQ ID NO:14, or an RNA equivalent or DNA/RNA chimeric thereof. In other embodiments, the first CFB-specific target-hybridizing sequence of (a) is SEQ ID NO:18, or an RNA equivalent or DNA/RNA chimeric thereof. Particularly suitable first (A) and second (B) CFB-specific target-hybridizing sequences of (a) include
(i) (A) SEQ ID NO:12, or an RNA equivalent or DNA/RNA chimeric thereof, and
(B) SEQ ID NO:13, or an RNA equivalent or DNA/RNA chimeric thereof;
(ii) (A) SEQ ID NO:12, or an RNA equivalent or DNA/RNA chimeric thereof, and
(B) SEQ ID NO:15, or an RNA equivalent or DNA/RNA chimeric thereof;
(iii) (A) SEQ ID NO:14, or an RNA equivalent or DNA/RNA chimeric thereof, and
(B) SEQ ID NO:15, or an RNA equivalent or DNA/RNA chimeric thereof; and
(iv) (A) SEQ ID NO:18, or an RNA equivalent or DNA/RNA chimeric thereof, and
(B) SEQ ID NO:15, or an RNA equivalent or DNA/RNA chimeric thereof.

In some variations, the composition further includes a CFB-specific detection probe oligomer comprising a CFB-specific detection probe target-hybridizing sequence that is from about 15 to about 35 nucleotides in length and is configured to hybridize to a target sequence contained within a CFB amplicon amplifiable by the first and second CFB-specific amplification oligomers. In some such embodiments, the first and second CFB-specific target-hybridizing sequences are the target-hybridizing sequences of (b) and the CFB-specific detection probe target-hybridizing sequence is SEQ ID NO:24, or an RNA equivalent or DNA/RNA chimeric thereof, the first and second CFB-specific target-hybridizing sequences are the target-hybridizing sequences of (d) and the CFB-specific detection probe target-hybridizing sequence is SEQ ID NO:25, or an RNA equivalent or DNA/RNA chimeric thereof, the first and second CFB-specific target-hybridizing sequences are the target-hybridizing sequences of (a) and the CFB-specific detection probe target-hybridizing sequence is SEQ ID NO:22 or SEQ ID NO:23, or an RNA equivalent or DNA/RNA chimeric thereof; or the first and second CFB-specific target-hybridizing sequences are the target-hybridizing sequences of (c) and the CFB-specific detection probe target-hybridizing sequence is SEQ ID NO:23, or an RNA equivalent or DNA/RNA chimeric thereof. In some variations, the CFB-specific detection probe oligomer further includes a detectable label such as, for example, a fluorescent or chemiluminescent label. In some embodiments comprising a detectably labeled probe oligomer, the detectable label is a fluorescent label and the CFB-specific detection probe oligomer further includes a non-fluorescent quencher. In some variations of a composition as above, the composition further includes a second amplification oligomer combination capable of amplifying a target region of a GBS SIP target nucleic acid.

In another aspect, the present invention provides an aqueous formulation for the amplification of GBS nucleic acid comprising a composition as above and an organic buffer. In some embodiments, the aqueous formulation further includes one or more components selected from a DNA polymerase enzyme, a reverse transcriptase enzyme, a detection probe oligomer, and a bulking agent (e.g., trehalose, raffinose, or a combination thereof). In some embodiments, the aqueous formulation contains inorganic salt at a concentration of 4 mM or less.

In another aspect, the present invention provides a reaction mixture for the amplification of GBS nucleic acid comprising an aqueous formulation as above.

In another aspect, the present invention provides a dried formulation for the amplification of GBS nucleic acid comprising a composition as above and a bulking agent. In some embodiments, the bulking agent is trehalose, raffinose, or a combination thereof. In some embodiments, the dried formulation further includes one or more components selected from an inorganic salt, a DNA polymerase enzyme, a reverse transcriptase enzyme, and a detection probe oligomer. In some embodiments further comprising an inorganic salt, the percent mass of the inorganic salt to the mass of the dried formulation is 0.249% or less. In certain variations, the dried formulation is a lyophilized formulation.

In another aspect, the present invention provides a reaction mixture for the amplification of GBS nucleic acid, where the reaction mixture is reconstituted with water or an organic buffer from a dried formulation as above. In some embodiments, the reaction mixture contains an inorganic salt such as, e.g., magnesium, potassium, or sodium; in some such variations, the concentration of the inorganic salt is 4 mM or less.

In another aspect, the present invention provides a kit for determining the presence or absence of GBS in a sample. In some embodiments, the kit includes at least one of a first amplification oligomer combination and a second amplification oligomer combination, where
(I) the first amplification oligomer combination includes first and second SIP-specific amplification oligomers capable of amplifying a target region of a GBS SIP target nucleic acid, where the first and second SIP-specific amplification oligomers comprise, respectively, first (A) and second (B) SIP-specific target-hybridizing sequences selected from
(a) (A) SEQ ID NO:3, or an RNA equivalent or DNA/RNA chimeric thereof, and
(B) SEQ ID NO:4, or an RNA equivalent or DNA/RNA chimeric thereof, and
(b) (A) SEQ ID NO:7, or an RNA equivalent or DNA/RNA chimeric thereof, and
(B) SEQ ID NO:8, or an RNA equivalent or DNA/RNA chimeric thereof,
and
(II) the second amplification oligomer combination includes first and second CFB-specific amplification oligomers capable of amplifying a target region of a GBS CFB target nucleic acid, where the first and second CFB-specific amplification oligomers comprise, respectively, first (A') and second (B') CFB-specific target-hybridizing sequences selected from (a) (A') a sequence that is from about 17 to about 24 contiguous nucleotides contained in the sequence of SEQ ID NO:26, or an RNA equivalent or DNA/RNA chimeric thereof, and
  (B') SEQ ID NO:13 or SEQ ID NO:15, or an RNA equivalent or DNA/RNA chimeric thereof;
(b) (A') SEQ ID NO:16, or an RNA equivalent or DNA/RNA chimeric thereof, and
  (B') SEQ ID NO:17, or an RNA equivalent or DNA/RNA chimeric thereof;
(c) (A') SEQ ID NO:18, or an RNA equivalent or DNA/RNA chimeric thereof, and
  (B') SEQ ID NO:15, or an RNA equivalent or DNA/RNA chimeric thereof; and
(d) (A') SEQ ID NO:20, or an RNA equivalent or DNA/RNA chimeric thereof, and
  (B') SEQ ID NO:21, or an RNA equivalent or DNA/RNA chimeric thereof.

In some embodiments of a kit as above where the kit includes the first amplification oligomer combination, the kit further includes a SIP-specific detection probe oligomer comprising a SIP-specific detection probe target-hybridizing sequence that is from about 15 to about 35 nucleotides in length and is configured to hybridize to a target sequence contained within a SIP amplicon amplifiable by the first and second SIP-specific amplification oligomers. In some such embodiments, the first and second SIP-specific target-hybridizing sequences are the target-hybridizing sequences of (I)(a) and the SIP-specific detection probe target-hybridizing sequence is SEQ ID NO:9, or an RNA equivalent or DNA/RNA chimeric thereof. In other embodiments, the first and second SIP-specific target-hybridizing sequences are the target-hybridizing sequences of (I)(b) and the SIP-specific detection probe target-hybridizing sequence is SEQ ID NO:11, or an RNA equivalent or DNA/RNA chimeric thereof. In some variations, the SIP-specific detection probe oligomer further includes a detectable label such as, for example, a fluorescent or chemiluminescent label. In some embodiments comprising a detectably labeled probe oligomer, the detectable label is a fluorescent label and the SIP-specific detection probe oligomer further includes a non-fluorescent quencher.

In some embodiments of a kit as above where the CFB-specific target-hybridizing sequences are the target-hybridizing sequences of (II)(a), the first CFB-specific target-hybridizing sequence of (II)(a) includes at least the sequence of SEQ ID NO:28, or an RNA equivalent or DNA/RNA chimeric thereof. In some such embodiments, the first CFB-specific target-hybridizing sequence of (II)(a) is contained in the sequence of SEQ ID NO:27, or an RNA equivalent or DNA/RNA chimeric thereof; in some such variations, the first CFB-specific target-hybridizing sequence of (II)(a) is SEQ ID NO:12 or SEQ ID NO:14, or an RNA equivalent or DNA/RNA chimeric thereof. In other embodiments where the CFB-specific target-hybridizing sequences are the target-hybridizing sequences of (II)(a), the first CFB-specific target-hybridizing sequence of (II)(a) is SEQ ID NO:18, or an RNA equivalent or DNA/RNA chimeric thereof. Particularly suitable first (A') and second (B') CFB-specific target-hybridizing sequences of (II)(a) include
  (i) (A') SEQ ID NO:12, or an RNA equivalent or DNA/RNA chimeric thereof, and
    (B') SEQ ID NO:13, or an RNA equivalent or DNA/RNA chimeric thereof;
  (ii) (A') SEQ ID NO:12, or an RNA equivalent or DNA/RNA chimeric thereof, and
    (B') SEQ ID NO:15, or an RNA equivalent or DNA/RNA chimeric thereof;
  (iii) (A') SEQ ID NO:14, or an RNA equivalent or DNA/RNA chimeric thereof, and
    (B') SEQ ID NO:15, or an RNA equivalent or DNA/RNA chimeric thereof; and
  (iv) (A') SEQ ID NO:18, or an RNA equivalent or DNA/RNA chimeric thereof, and
    (B') SEQ ID NO:15, or an RNA equivalent or DNA/RNA chimeric thereof.

In some embodiments of a kit as above where the kit includes the first amplification oligomer combination, the kit further comprises a CFB-specific detection probe oligomer comprising a CFB-specific detection probe target-hybridizing sequence that is from about 15 to about 35 nucleotides in length and is configured to hybridize to a target sequence contained within a CFB amplicon amplifiable by the first and second CFB-specific amplification oligomers. In some such embodiments, the first and second CFB-specific target-hybridizing sequences are the target-hybridizing sequences of (II)(b) and the CFB-specific detection probe target-hybridizing sequence is SEQ ID NO:24, or an RNA equivalent or DNA/RNA chimeric thereof; the first and second CFB-specific target-hybridizing sequences are the target-hybridizing sequences of (II)(d) and the CFB-specific detection probe target-hybridizing sequence is SEQ ID NO:25, or an RNA equivalent or DNA/RNA chimeric thereof; the first and second CFB-specific target-hybridizing sequences are the target-hybridizing sequences of (II)(a) and the CFB-specific detection probe target-hybridizing sequence is SEQ ID NO:22 or SEQ ID NO:23, or an RNA equivalent or DNA/RNA chimeric thereof; or the first and second CFB-specific target-hybridizing sequences are the target-hybridizing sequences of (II)(c) and the CFB-specific detection probe target-hybridizing sequence is SEQ ID NO:23, or an RNA equivalent or DNA/RNA chimeric thereof. In some variations, the CFB-specific detection probe oligomer further includes a detectable label such as, for example, a fluorescent or chemiluminescent label. In some embodiments comprising a detectably labeled probe oligomer, the detectable label is a fluorescent label and the CFB-specific detection probe oligomer further includes a non-fluorescent quencher.

In certain embodiments of a kit for determining the presence or absence of GBS in a sample as above, the kit includes both the first and second amplification oligomer combinations.

In another aspect, the present invention provides a kit for determining the presence or absence of GBS in a sample, where the kit includes an amplification oligomer combination comprising first and second SIP-specific amplification oligomers capable of amplifying a target region of a GBS SIP target nucleic acid. Particularly suitable first and second SIP-specific amplification oligomers comprise, respectively, first (A) and second (B) SIP-specific target-hybridizing sequences selected from
  (a) (A) SEQ ID NO:3, or an RNA equivalent or DNA/RNA chimeric thereof, and
    (B) SEQ ID NO:4, or an RNA equivalent or DNA/RNA chimeric thereof, and
  (b) (A) SEQ ID NO:7, or an RNA equivalent or DNA/RNA chimeric thereof, and
    (B) SEQ ID NO:8, or an RNA equivalent or DNA/RNA chimeric thereof.

In some variations, the kit further includes a SIP-specific detection probe oligomer comprising a SIP-specific detection probe target-hybridizing sequence that is from about 15 to about 35 nucleotides in length and is configured to hybridize to a target sequence contained within a SIP amplicon amplifiable by the first and second SIP-specific amplification oligomers. In some such embodiments, the first and second SIP-specific target-hybridizing sequences are the target-hybridizing sequences of (a) and the SIP-specific detection probe target-hybridizing sequence is SEQ ID NO:9, or an RNA equivalent or DNA/RNA chimeric thereof. In other embodiments, the first and second SIP-specific target-hybridizing sequences are the target-hybridizing sequences of (b) and the SIP-specific detection probe target-hybridizing sequence is SEQ ID NO:11, or an RNA equivalent or DNA/RNA chimeric thereof. In some variations, the SIP-specific detection probe oligomer further includes a detectable label such as, for example, a fluorescent or chemiluminescent label. In some embodiments comprising a detectably labeled probe oligomer, the detectable label is a fluorescent label and the SIP-specific detection probe oligomer further includes a non-fluorescent quencher. In some variations of a kit as above, the kit further includes a second amplification oligomer combination capable of amplifying a target region of a GBS CFB target nucleic acid.

In another aspect, the present invention provides a kit for determining the presence or absence of GBS in a sample, where the kit includes an amplification oligomer combination comprising first and second CFB-specific amplification oligomers capable of amplifying a target region of a GBS CFB target nucleic acid. Particularly suitable first and second CFB-specific amplification oligomers comprise, respectively, first (A) and second (B) CFB-specific target-hybridizing sequences selected from (a) (A) a sequence that is from about 17 to about 24 contiguous nucleotides contained in the sequence of SEQ ID NO:26, or an RNA equivalent or DNA/RNA chimeric thereof, and (B) SEQ ID NO:13 or SEQ ID NO:15, or an RNA equivalent or DNA/RNA chimeric thereof;

(b) (A) SEQ ID NO:16, or an RNA equivalent or DNA/RNA chimeric thereof, and (B) SEQ ID NO:17, or an RNA equivalent or DNA/RNA chimeric thereof;

(c) (A) SEQ ID NO:18, or an RNA equivalent or DNA/RNA chimeric thereof, and (B) SEQ ID NO:15, or an RNA equivalent or DNA/RNA chimeric thereof; and (d) (A) SEQ ID NO:20, or an RNA equivalent or DNA/RNA chimeric thereof, and (B) SEQ ID NO:21, or an RNA equivalent or DNA/RNA chimeric thereof.

In certain embodiments, the first CFB-specific target-hybridizing sequence of (a) includes at least the sequence of SEQ ID NO:28, or an RNA equivalent or DNA/RNA chimeric thereof. In some such embodiments, the first CFB-specific target-hybridizing sequence of (a) is contained in the sequence of SEQ ID NO:27, or an RNA equivalent or DNA/RNA chimeric thereof, in some such variations, the first CFB-specific target-hybridizing sequence of (a) is SEQ ID NO:12 or SEQ ID NO:14, or an RNA equivalent or DNA/RNA chimeric thereof. In other embodiments, the first CFB-specific target-hybridizing sequence of (a) is SEQ ID NO:18, or an RNA equivalent or DNA/RNA chimeric thereof. Particularly suitable first (A) and second (B) CFB-specific target-hybridizing sequences of (a) include (i) (A) SEQ ID NO:12, or an RNA equivalent or DNA/RNA chimeric thereof, and
(B) SEQ ID NO:13, or an RNA equivalent or DNA/RNA chimeric thereof;

(ii) (A) SEQ ID NO:12, or an RNA equivalent or DNA/RNA chimeric thereof, and
(B) SEQ ID NO:15, or an RNA equivalent or DNA/RNA chimeric thereof;

(iii) (A) SEQ ID NO:14, or an RNA equivalent or DNA/RNA chimeric thereof, and
(B) SEQ ID NO:15, or an RNA equivalent or DNA/RNA chimeric thereof; and (iv) (A) SEQ ID NO:18, or an RNA equivalent or DNA/RNA chimeric thereof, and
(B) SEQ ID NO:15, or an RNA equivalent or DNA/RNA chimeric thereof.

In some variations, the kit further includes a CFB-specific detection probe oligomer comprising a CFB-specific detection probe target-hybridizing sequence that is from about 15 to about 35 nucleotides in length and is configured to hybridize to a target sequence contained within a CFB amplicon amplifiable by the first and second CFB-specific amplification oligomers. In some such embodiments, the first and second CFB-specific target-hybridizing sequences are the target-hybridizing sequences of (b) and the CFB-specific detection probe target-hybridizing sequence is SEQ ID NO:24, or an RNA equivalent or DNA/RNA chimeric thereof, the first and second CFB-specific target-hybridizing sequences are the target-hybridizing sequences of (d) and the CFB-specific detection probe target-hybridizing sequence is SEQ ID NO:25, or an RNA equivalent or DNA/RNA chimeric thereof, the first and second CFB-specific target-hybridizing sequences are the target-hybridizing sequences of (a) and the CFB-specific detection probe target-hybridizing sequence is SEQ ID NO:22 or SEQ ID NO:23, or an RNA equivalent or DNA/RNA chimeric thereof, or the first and second CFB-specific target-hybridizing sequences are the target-hybridizing sequences of (c) and the CFB-specific detection probe target-hybridizing sequence is SEQ ID NO:23, or an RNA equivalent or DNA/RNA chimeric thereof. In some variations, the CFB-specific detection probe oligomer further includes a detectable label such as, for example, a fluorescent or chemiluminescent label. In some embodiments comprising a detectably labeled probe oligomer, the detectable label is a fluorescent label and the CFB-specific detection probe oligomer further includes a non-fluorescent quencher. In some variations of a kit as above, the kit further includes a second amplification oligomer combination capable of amplifying a target region of a GBS SIP target nucleic acid.

In another aspect, the present invention provides a method for determining the presence or absence of GBS in a sample. In some embodiments, the method includes
(1) contacting a sample suspected of containing GBS with at least one of a first amplification oligomer combination and a second amplification oligomer combination, where
(I) the first amplification oligomer combination includes first and second SIP-specific amplification oligomers for amplifying a target region of a GBS SIP target nucleic acid, where the first and second SIP-specific amplification oligomers comprise, respectively, first (A) and second (B) SIP-specific target-hybridizing sequences selected from
(a) (A) SEQ ID NO:3, or an RNA equivalent or DNA/RNA chimeric thereof, and
  (B) SEQ ID NO:4, or an RNA equivalent or DNA/RNA chimeric thereof; and
(b) (A) SEQ ID NO:7, or an RNA equivalent or DNA/RNA chimeric thereof, and
  (B) SEQ ID NO:8, or an RNA equivalent or DNA/RNA chimeric thereof;
and
(II) the second amplification oligomer combination includes first and second CFB-specific amplification oligomers for amplifying a target region of a GBS CFB target nucleic acid, where the first and second CFB-specific amplification oligomers comprise, respectively, first (A') and second (B') CFB-specific target-hybridizing sequences selected from
(a) (A') a sequence that is from about 17 to about 24 contiguous nucleotides contained in the sequence of SEQ ID NO:26, or an RNA equivalent or DNA/RNA chimeric thereof, and
  (B') SEQ ID NO:13 or SEQ ID NO:15, or an RNA equivalent or DNA/RNA chimeric thereof;
(b) (A') SEQ ID NO:16, or an RNA equivalent or DNA/RNA chimeric thereof, and
  (B') SEQ ID NO:17, or an RNA equivalent or DNA/RNA chimeric thereof;
(c) (A') SEQ ID NO:18, or an RNA equivalent or DNA/RNA chimeric thereof, and
  (B') SEQ ID NO:15, or an RNA equivalent or DNA/RNA chimeric thereof; and
(d) (A') SEQ ID NO:20, or an RNA equivalent or DNA/RNA chimeric thereof, and
  (B') SEQ ID NO:21, or an RNA equivalent or DNA/RNA chimeric thereof;
(2) performing an in vitro nucleic acid amplification reaction, where any GBS SIP and/or CFB target nucleic acid, if present in the sample, is used as a template for generating one or more amplicons corresponding to at least one of the SIP and CFB target regions; and
(3) detecting the presence or absence of the one or more amplicons, thereby determining the presence or absence of GBS in the sample.

In some embodiments of a method as above, the method includes contacting the sample with both the first and second amplification oligomer combinations. In some such embodiments, the method is a multiplex method comprising contacting the sample with both the first and second amplification oligomer combinations within the same reaction mixture.

In some embodiments of a method as above where the method includes contacting the sample with the first amplification oligomer combination, the detecting step includes contacting the in vitro nucleic acid amplification reaction with a SIP-specific detection probe oligomer comprising a SIP-specific detection probe target-hybridizing sequence that is from about 15 to about 35 nucleotides in length and is configured to hybridize to a target sequence contained within a SIP amplicon amplifiable by the first and second SIP-specific amplification oligomers. In some such embodiments, the first and second SIP-specific target-hybridizing sequences are the target-hybridizing sequences of (I)(a) and the SIP-specific detection probe target-hybridizing sequence is SEQ ID NO:9, or an RNA equivalent or DNA/RNA chimeric thereof. In other embodiments, the first and second SIP-specific target-hybridizing sequences are the target-hybridizing sequences of (I)(b) and the SIP-specific detection probe target-hybridizing sequence is SEQ ID NO:11, or an RNA equivalent or DNA/RNA chimeric thereof. In some variations, the SIP-specific detection probe oligomer further includes a detectable label such as, for example, a fluorescent or chemiluminescent label. In some embodiments comprising a detectably labeled probe oligomer, the detectable label is a fluorescent label and the SIP-specific detection probe oligomer further includes a non-fluorescent quencher.

In some embodiments of a method as above where the CFB-specific target-hybridizing sequences are the target-hybridizing sequences of (II)(a), the first CFB-specific target-hybridizing sequence of (II)(a) includes at least the sequence of SEQ ID NO:28, or an RNA equivalent or DNA/RNA chimeric thereof. In some such embodiments, the first CFB-specific target-hybridizing sequence of (II)(a) is contained in the sequence of SEQ ID NO:27, or an RNA equivalent or DNA/RNA chimeric thereof; in some such variations, the first CFB-specific target-hybridizing sequence of (II)(a) is SEQ ID NO:12 or SEQ ID NO:14, or an RNA equivalent or DNA/RNA chimeric thereof. In other embodiments where the CFB-specific target-hybridizing sequences are the target-hybridizing sequences of (II)(a), the first CFB-specific target-hybridizing sequence of (II)(a) is SEQ ID NO:18, or an RNA equivalent or DNA/RNA chimeric thereof. Particularly suitable first (A') and second (B') CFB-specific target-hybridizing sequences of (II)(a) include
(i) (A') SEQ ID NO:12, or an RNA equivalent or DNA/RNA chimeric thereof, and
  (B') SEQ ID NO:13, or an RNA equivalent or DNA/RNA chimeric thereof,
(ii) (A') SEQ ID NO:12, or an RNA equivalent or DNA/RNA chimeric thereof, and
  (B') SEQ ID NO:15, or an RNA equivalent or DNA/RNA chimeric thereof;
(iii) (A') SEQ ID NO:14, or an RNA equivalent or DNA/RNA chimeric thereof, and
  (B') SEQ ID NO:15, or an RNA equivalent or DNA/RNA chimeric thereof; and
(iv) (A') SEQ ID NO:18, or an RNA equivalent or DNA/RNA chimeric thereof, and
  (B') SEQ ID NO:15, or an RNA equivalent or DNA/RNA chimeric thereof.

In some embodiments of a method as above where the method includes contacting the sample with the second amplification oligomer combination, the detecting step includes contacting the in vitro nucleic acid amplification reaction with a CFB-specific detection probe oligomer comprising a CFB-specific detection probe target-hybridizing sequence that is from about 15 to about 35 nucleotides in length and is configured to hybridize to a target sequence contained within a CFB amplicon amplifiable by the first and second CFB-specific amplification oligomers. In some such embodiments, the first and second CFB-specific target-hybridizing sequences are the target-hybridizing sequences of (II)(b) and the CFB-specific detection probe target-hybridizing sequence is SEQ ID NO:24, or an RNA equivalent or DNA/RNA chimeric thereof; the first and second CFB-specific target-hybridizing sequences are the target-hybridizing sequences of (II)(d) and the CFB-specific detection probe target-hybridizing sequence is SEQ ID NO:25, or an RNA equivalent or DNA/RNA chimeric thereof; the first and second CFB-specific target-hybridizing sequences are the target-hybridizing sequences of (II)(a) and the CFB-specific detection probe target-hybridizing sequence is SEQ ID NO:22 or SEQ ID NO:23, or an RNA equivalent or DNA/

RNA chimeric thereof; or the first and second CFB-specific target-hybridizing sequences are the target-hybridizing sequences of (II)(c) and the CFB-specific detection probe target-hybridizing sequence is SEQ ID NO:23, or an RNA equivalent or DNA/RNA chimeric thereof. In some variations, the CFB-specific detection probe oligomer further includes a detectable label such as, for example, a fluorescent or chemiluminescent label. In some embodiments comprising a detectably labeled probe oligomer, the detectable label is a fluorescent label and the CFB-specific detection probe oligomer further includes a non-fluorescent quencher.

In certain variations of a method for determining the presence or absence of GBS in a sample as above, the detecting step is performed in real time.

In certain variations of a method for determining the presence or absence of GBS in a sample as above, the in vitro nucleic acid amplification reaction is a PCR amplification reaction (e.g., a real-time PCR amplification reaction).

In some embodiments of a method as above where the method includes contacting the sample with both the first and second amplification oligomer combinations (e.g., a multiplex method), the detecting step includes contacting the in vitro nucleic acid amplification reaction with (i) a SIP-specific detection probe oligomer comprising a SIP-specific detection probe target-hybridizing sequence that is from about 15 to about 35 nucleotides in length and is configured to hybridize to a target sequence contained within a SIP amplicon amplifiable by the first and second SIP-specific amplification oligomers, and (ii) a CFB-specific detection probe oligomer comprising a CFB-specific detection probe target-hybridizing sequence that is from about 15 to about 35 nucleotides in length and is configured to hybridize to a target sequence contained within a CFB amplicon amplifiable by the first and second CFB-specific amplification oligomers, where each of the SIP-specific and CFB-specific detection probe oligomers includes a fluorescent label and a non-fluorescent quencher. In some such embodiments, the in vitro nucleic acid amplification reaction is a real-time PCR amplification reaction.

In another aspect, the present invention provides a method for determining the presence or absence of GBS in a sample, where the method includes
(1) contacting a sample suspected of containing GBS with an amplification oligomer combination comprising first and second SIP-specific amplification oligomers for amplifying a target region of a GBS SIP target nucleic acid, where the first and second SIP-specific amplification oligomers comprise, respectively, first (A) and second (B) SIP-specific target-hybridizing sequences selected from
  (a) (A) SEQ ID NO:3, or an RNA equivalent or DNA/RNA chimeric thereof, and
    (B) SEQ ID NO:4, or an RNA equivalent or DNA/RNA chimeric thereof; and
  (b) (A) SEQ ID NO:7, or an RNA equivalent or DNA/RNA chimeric thereof, and
    (B) SEQ ID NO:8, or an RNA equivalent or DNA/RNA chimeric thereof;
(2) performing an in vitro nucleic acid amplification reaction, where any GBS SIP target nucleic acid, if present in the sample, is used as a template for generating an amplicon corresponding to the SIP target region; and
(3) detecting the presence or absence of the amplicon, thereby determining the presence or absence of GBS in the sample.

In some variations, the detecting step comprises contacting the in vitro nucleic acid amplification reaction with a SIP-specific detection probe oligomer comprising a SIP-specific detection probe target-hybridizing sequence that is from about 15 to about 35 nucleotides in length and is configured to hybridize to a target sequence contained within a SIP amplicon amplifiable by the first and second SIP-specific amplification oligomers. In some such embodiments, the first and second SIP-specific target-hybridizing sequences are the target-hybridizing sequences of (a) and the SIP-specific detection probe target-hybridizing sequence is SEQ ID NO:9, or an RNA equivalent or DNA/RNA chimeric thereof. In other embodiments, the first and second SIP-specific target-hybridizing sequences are the target-hybridizing sequences of (b) and the SIP-specific detection probe target-hybridizing sequence is SEQ ID NO:11, or an RNA equivalent or DNA/RNA chimeric thereof. In some variations, the SIP-specific detection probe oligomer further includes a detectable label such as, for example, a fluorescent or chemiluminescent label. In some embodiments comprising a detectably labeled probe oligomer, the detectable label is a fluorescent label and the SIP-specific detection probe oligomer further includes a non-fluorescent quencher. In certain variations, the detecting step is performed in real time. In certain variations, the in vitro nucleic acid amplification reaction is a PCR amplification reaction (e.g., a real-time PCR amplification reaction). In some embodiments, the method further includes contacting the sample with a second amplification oligomer combination comprising first and second CFB-specific amplification oligomers for amplifying a target region of a GBS CFB target nucleic acid, where, at the amplification step, any GBS CFB target nucleic acid, if present in the sample, is used as a template for generating an amplicon corresponding to the CFB target region, and where the detecting step includes detecting the presence or absence of the amplicon corresponding to the CFB target region.

In another aspect, the present invention provides a method for determining the presence or absence of GBS in a sample, where the method includes
(1) contacting a sample suspected of containing GBS with an amplification oligomer combination comprising first and second CFB-specific amplification oligomers for amplifying a target region of a GBS CFB target nucleic acid, where the first and second CFB-specific amplification oligomers comprise, respectively, first (A) and second (B) CFB-specific target-hybridizing sequences selected from
  (a) (A) a sequence that is from about 17 to about 24 contiguous nucleotides contained in the sequence of SEQ ID NO:26, or an RNA equivalent or DNA/RNA chimeric thereof, and
    (B) SEQ ID NO:13 or SEQ ID NO:15, or an RNA equivalent or DNA/RNA chimeric thereof;
  (b) (A) SEQ ID NO:16, or an RNA equivalent or DNA/RNA chimeric thereof, and
    (B) SEQ ID NO:17, or an RNA equivalent or DNA/RNA chimeric thereof,
  (c) (A) SEQ ID NO:18, or an RNA equivalent or DNA/RNA chimeric thereof, and
    (B) SEQ ID NO:15, or an RNA equivalent or DNA/RNA chimeric thereof; and
  (d) (A) SEQ ID NO:20, or an RNA equivalent or DNA/RNA chimeric thereof, and
    (B) SEQ ID NO:21, or an RNA equivalent or DNA/RNA chimeric thereof;

(2) performing an in vitro nucleic acid amplification reaction, where any GBS CFB target nucleic acid, if present in the sample, is used as a template for generating an amplicon corresponding to the CFB target region; and (3) detecting the presence or absence of the amplicon, thereby determining the presence or absence of GBS in the sample.

In certain embodiments, the first CFB-specific target-hybridizing sequence of (a) includes at least the sequence of SEQ ID NO:28, or an RNA equivalent or DNA/RNA chimeric thereof. In some such embodiments, the first CFB-specific target-hybridizing sequence of (a) is contained in the sequence of SEQ ID NO:27, or an RNA equivalent or DNA/RNA chimeric thereof, in some such variations, the first CFB-specific target-hybridizing sequence of (a) is SEQ ID NO:12 or SEQ ID NO:14, or an RNA equivalent or DNA/RNA chimeric thereof. In other embodiments, the first CFB-specific target-hybridizing sequence of (a) is SEQ ID NO:18, or an RNA equivalent or DNA/RNA chimeric thereof. Particularly suitable first (A) and second (B) CFB-specific target-hybridizing sequences of (a) include (i) (A) SEQ ID NO:12, or an RNA equivalent or DNA/RNA chimeric thereof, and
(B) SEQ ID NO:13, or an RNA equivalent or DNA/RNA chimeric thereof;
(ii) (A) SEQ ID NO:12, or an RNA equivalent or DNA/RNA chimeric thereof, and
(B) SEQ ID NO:15, or an RNA equivalent or DNA/RNA chimeric thereof;
(iii) (A) SEQ ID NO:14, or an RNA equivalent or DNA/RNA chimeric thereof, and
(B) SEQ ID NO:15, or an RNA equivalent or DNA/RNA chimeric thereof; and
(iv) (A) SEQ ID NO:18, or an RNA equivalent or DNA/RNA chimeric thereof, and
(B) SEQ ID NO:15, or an RNA equivalent or DNA/RNA chimeric thereof.

In some variations, the detecting step includes contacting the in vitro nucleic acid amplification reaction with a CFB-specific detection probe target-hybridizing sequence that is from about 15 to about 35 nucleotides in length and is configured to hybridize to a target sequence contained within a CFB amplicon amplifiable by the first and second CFB-specific amplification oligomers. In some such embodiments, the first and second CFB-specific target-hybridizing sequences are the target-hybridizing sequences of (b) and the CFB-specific detection probe target-hybridizing sequence is SEQ ID NO:24, or an RNA equivalent or DNA/RNA chimeric thereof, the first and second CFB-specific target-hybridizing sequences are the target-hybridizing sequences of (d) and the CFB-specific detection probe target-hybridizing sequence is SEQ ID NO:25, or an RNA equivalent or DNA/RNA chimeric thereof; the first and second CFB-specific target-hybridizing sequences are the target-hybridizing sequences of (a) and the CFB-specific detection probe target-hybridizing sequence is SEQ ID NO:22 or SEQ ID NO:23, or an RNA equivalent or DNA/RNA chimeric thereof, or the first and second CFB-specific target-hybridizing sequences are the target-hybridizing sequences of (c) and the CFB-specific detection probe target-hybridizing sequence is SEQ ID NO:23, or an RNA equivalent or DNA/RNA chimeric thereof. In some variations, the CFB-specific detection probe oligomer further includes a detectable label such as, for example, a fluorescent or chemiluminescent label. In some embodiments comprising a detectably labeled probe oligomer, the detectable label is a fluorescent label and the CFB-specific detection probe oligomer further includes a non-fluorescent quencher. In certain variations, the detecting step is performed in real time. In certain variations, the in vitro nucleic acid amplification reaction is a PCR amplification reaction (e.g., a real-time PCR amplification reaction). In some embodiments, the method further includes contacting the sample with a second amplification oligomer combination comprising first and second SIP-specific amplification oligomers for amplifying a target region of a GBS SIP target nucleic acid, where, at the amplification step, any GBS SIP target nucleic acid, if present in the sample, is used as a template for generating an amplicon corresponding to the SIP target region, and where the detecting step comprises detecting the presence or absence of the amplicon corresponding to the SIP target region.

In some embodiments of a method for as above for determining the presence or absence of GBS in a sample, the method determines the presence or absence of any of GBS serotypes Ia, Ib, Ic, II, III, IV, V, VI, VII, VIII, and IX. In some such embodiments, the method further determines the presence or absence of a non-hemolytic strain of GBS.

In another aspect, the present invention provides a detection probe oligomer. In some embodiments, the detection probe oligomer is a SIP-specific detection probe oligomer comprising a SIP-specific detection probe target-hybridizing sequence that is from about 15 to about 35 nucleotides in length and is configured to hybridize to a target sequence contained within a SIP amplicon amplifiable by a first amplification oligomer combination comprises first and second SIP-specific amplification oligomers capable of amplifying a target region of a GBS SIP target nucleic acid, wherein the first and second SIP-specific amplification oligomers comprise, respectively, first (A) and second (B) SIP-specific target-hybridizing sequences selected from the group consisting of (a) (A) SEQ ID NO:3, or an RNA equivalent or DNA/RNA chimeric thereof, and
(B) SEQ ID NO:4, or an RNA equivalent or DNA/RNA chimeric thereof, and
(b) (A) SEQ ID NO:7, or an RNA equivalent or DNA/RNA chimeric thereof, and
(B) SEQ ID NO:8, or an RNA equivalent or DNA/RNA chimeric thereof.

In some embodiments of a SIP-specific detection probe oligomer as above, the SIP-specific detection probe target-hybridizing sequence is selected from (a) SEQ ID NO:9, or an RNA equivalent or DNA/RNA chimeric thereof, and (b) SEQ ID NO:11, or an RNA equivalent or DNA/RNA chimeric thereof. In some variations, the SIP-specific detection probe oligomer further includes a detectable label such as, for example, a fluorescent or chemiluminescent label. In some embodiments comprising a detectably labeled probe oligomer, the detectable label is a fluorescent label and the SIP-specific detection probe oligomer further includes a non-fluorescent quencher.

In other embodiments, the detection probe oligomer is a CFB-specific detection probe oligomer comprising a CFB-specific detection probe target-hybridizing sequence that is from about 15 to about 35 nucleotides in length and is configured to hybridize to a target sequence contained within a CFB amplicon amplifiable by a second amplification oligomer combination comprises first and second CFB-specific amplification oligomers capable of amplifying a target region of a GBS CFB target nucleic acid, wherein the first and second CFB-specific amplification oligomers comprise, respectively, first (A') and second (B') CFB-specific target-hybridizing sequences selected from
(a) (A') a sequence that is from about 17 to about 24 contiguous nucleotides contained in the sequence of SEQ ID NO:26, or an RNA equivalent or DNA/RNA chimeric thereof, and
(B') SEQ ID NO:13 or SEQ ID NO:15, or an RNA equivalent or DNA/RNA chimeric thereof;
(b) (A') SEQ ID NO:16, or an RNA equivalent or DNA/RNA chimeric thereof, and
(B') SEQ ID NO:17, or an RNA equivalent or DNA/RNA chimeric thereof;
(c) (A') SEQ ID NO:18, or an RNA equivalent or DNA/RNA chimeric thereof, and
(B') SEQ ID NO:15, or an RNA equivalent or DNA/RNA chimeric thereof; and
(d) (A') SEQ ID NO:20, or an RNA equivalent or DNA/RNA chimeric thereof, and
(B') SEQ ID NO:21, or an RNA equivalent or DNA/RNA chimeric thereof.

In some embodiments of a CFB-specific detection probe oligomer as above, the CFB-specific detection probe target-hybridizing sequence is selected from (a) SEQ ID NO:24, or an RNA equivalent or DNA/RNA chimeric thereof, (b) SEQ ID NO:25, or an RNA equivalent or DNA/RNA chimeric thereof, (c) SEQ ID NO:22, or an RNA equivalent or DNA/RNA chimeric thereof, and (d) SEQ ID NO:23, or an RNA equivalent or DNA/RNA chimeric thereof. In some variations, the CFB-specific detection probe oligomer further includes a detectable label such as, for example, a fluorescent or chemiluminescent label. In some embodiments comprising a detectably labeled probe oligomer, the detectable label is a fluorescent label and the CFB-specific detection probe oligomer further includes a non-fluorescent quencher.

In another aspect, the present invention provides a composition comprising a SIP-specific detection probe oligomer and a CFB-specific detection probe oligomer as above.

In another aspect, the present invention provides an aqueous formulation for the detection of GBS nucleic acid comprising (1) a SIP-specific detection probe oligomer and/or a CFB-specific detection probe oligomer as above and (2) an organic buffer. In some embodiments, the aqueous formulation further includes one or more components selected from a surfactant (e.g., polyethylene glycol mono [4-(1,1,3,3-tetramethylbutyl) phenyl] ether, polysorbate 20, or a combination thereof), a DNA polymerase enzyme, a reverse transcriptase enzyme, at least one amplification oligomer, and a bulking agent (e.g., trehalose, raffinose, or a combination thereof). In certain variations comprising a surfactant, the surfactant is a non-linear surfactant such as, for example, polysorbate 20. In some embodiments, the aqueous formulation contains inorganic salt at a concentration of 4 mM or less. In a related aspect, the present invention provides a reaction mixture for the detection of GBS comprising an aqueous formulation as above.

In another aspect, the present invention provides a dried formulation for the detection of GBS nucleic acid comprising (1) a SIP-specific detection probe oligomer and/or a CFB-specific detection probe oligomer as above and (2) a bulking agent. In some embodiments, the bulking agent is trehalose, raffinose, or a combination thereof. In some embodiments, the dried formulation further includes one or more components selected from an inorganic salt, a DNA polymerase enzyme, a reverse transcriptase enzyme, at least one amplification oligomer, and a surfactant (e.g., polyethylene glycol mono [4-(1,1,3,3-tetramethylbutyl) phenyl] ether, polysorbate 20, or a combination thereof). In some embodiments further comprising an inorganic salt, the percent mass of the inorganic salt to the mass of the dried formulation is 0.249% or less. In certain variations comprising a surfactant, the surfactant is a non-linear surfactant such as, for example, polysorbate 20. In certain variations, the dried formulation is a lyophilized formulation. In a related aspect, the present invention provides a reaction mixture for the detection of GBS, where the reaction mixture is reconstituted with water and an organic buffer from a dried formulation as above. In some embodiments, the reaction mixture contains an inorganic salt such as, e.g., magnesium, potassium, or sodium; in some such variations, the concentration of the inorganic salt is 4 mM or less.

These and other aspects of the invention will become evident upon reference to the following detailed description of the invention and the attached drawings.

DEFINITIONS

Unless defined otherwise, all technical and scientific terms used herein have the same meaning as commonly understood by one of ordinary skill in the art pertinent to the methods and compositions described. General definitions may be found in technical books relevant to the art of molecular biology, e.g., Dictionary of Microbiology and Molecular Biology, 2nd ed. (Singleton et al., 1994, John Wiley & Sons, New York, N.Y.) or The Harper Collins Dictionary of Biology (Hale & Marham, 1991, Harper Perennial, New York, N.Y.). As used herein, the following terms and phrases have the meanings ascribed to them unless specified otherwise.

The terms "a," "an," and "the" include plural referents, unless the context clearly indicates otherwise. For example, "a nucleic acid" as used herein is understood to represent one or more nucleic acids. As such, the terms "a" (or "an"), "one or more," and "at least one" can be used interchangeably herein.

It will be appreciated that there is an implied "about" prior to the temperatures, concentrations, times, etc. discussed in the present disclosure, such that slight and insubstantial deviations are within the scope of the present teachings herein. In general, the term "about" indicates insubstantial variation in a quantity of a component of a composition not having any significant effect on the activity or stability of the composition. All ranges are to be interpreted as encompassing the endpoints in the absence of express exclusions such as "not including the endpoints"; thus, for example, "within 10-15" includes the values 10 and 15. Also, the use of "comprise," "comprises," "comprising," "contain," "contains," "containing," "include," "includes," and "including" are not intended to be limiting. It is to be understood that both the foregoing general description and detailed description are exemplary and explanatory only and are not restrictive of the teachings. To the extent that any material incorporated by reference is inconsistent with the express content of this disclosure, the express content controls.

Unless specifically noted, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims). "Consisting essentially of" means that additional component(s), composition(s) or method step(s) that do not materially change the basic and novel characteristics of the compositions and methods described herein may be included in those compositions or methods. Such characteristics include the ability to detect a Group B *Streptococcus* (GBS) nucleic acid sequence present in a sample with specificity that distinguishes the GBS nucleic acid from other known pathogens, optionally at a sensitivity that can detect the bacterium present in a sample at a concentration of about 100 CFU/ml, and, optionally within about 60 minutes and/or within about 40 cycles from the beginning of an amplification reaction when a cycled amplification reaction is used.

"Sample" includes any specimen that may contain GBS or components thereof, such as nucleic acids or fragments of nucleic acids. Samples include "biological samples" which include any tissue or material derived from a living or dead human that may contain GBS or target nucleic acid derived therefrom, including, e.g., vaginal swab samples, cervical brush samples, respiratory tissue or exudates such as bronchoscopy, bronchoalveolar lavage (BAL) or lung biopsy, sputum, saliva, peripheral blood, plasma, serum, lymph node, gastrointestinal tissue, feces, urine, semen or other body fluids or materials. The biological sample may be treated to physically or mechanically disrupt tissue or cell structure, thus releasing intracellular components into a solution which may further contain enzymes, buffers, salts, detergents and the like, which are used to prepare, using standard methods, a biological sample for analysis. Also, samples may include processed samples, such as those obtained from passing samples over or through a filtering device, or following centrifugation, or by adherence to a medium, matrix, or support.

"Nucleic acid" and "polynucleotide" refer to a multimeric compound comprising nucleosides or nucleoside analogs which have nitrogenous heterocyclic bases or base analogs linked together to form a polynucleotide, including conventional RNA, DNA, mixed RNA-DNA, and polymers that are analogs thereof. A nucleic acid "backbone" may be made up of a variety of linkages, including one or more of sugar-phosphodiester linkages, peptide-nucleic acid bonds ("peptide nucleic acids" or PNA; PCT Publication No. WO 95/32305), phosphorothioate linkages, methylphosphonate linkages, or combinations thereof. Sugar moieties of a nucleic acid may be ribose, deoxyribose, or similar compounds with substitutions, e.g., 2' methoxy or 2' halide substitutions. Nitrogenous bases may be conventional bases (A, G, C, T, U), analogs thereof (e.g., inosine or others; see *The Biochemistry of the Nucleic Acids* 5-36, Adams et al., ed., 11th ed., 1992), derivatives of purines or pyrimidines (e.g., $N^4$-methyl deoxyguanosine, deaza- or aza-purines, deaza- or aza-pyrimidines, pyrimidine bases with substituent groups at the 5 or 6 position, purine bases with a substituent at the 2, 6, or 8 positions, 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines; U.S. Pat. No. 5,378,825 and PCT Publication No. WO 93/13121). Nucleic acids may include one or more "abasic" residues where the backbone includes no nitrogenous base for position(s) of the polymer (U.S. Pat. No. 5,585,481). A nucleic acid may comprise only conventional RNA or DNA sugars, bases and linkages, or may include both conventional components and substitutions (e.g., conventional bases with 2' methoxy linkages, or polymers containing both conventional bases and one or more base analogs). Nucleic acid includes "locked nucleic acid" (LNA), an analogue containing one or more LNA nucleotide monomers with a bicyclic furanose unit locked in an RNA mimicking sugar conformation, which enhance hybridization affinity toward complementary RNA and DNA sequences (Vester and Wengel, 2004, *Biochemistry* 43(42): 13233-41). Embodiments of oligomers that may affect stability of a hybridization complex include PNA oligomers, oligomers that include 2'-methoxy or 2'-fluoro substituted RNA, or oligomers that affect the overall charge, charge density, or steric associations of a hybridization complex, including oligomers that contain charged linkages (e.g., phosphorothioates) or neutral groups (e.g., methylphosphonates). 5-methylcytosines may be used in conjunction with any of the foregoing backbones/sugars/linkages including RNA or DNA backbones (or mixtures thereof) unless otherwise indicated. It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24, and 25).

A "nucleotide" as used herein is a subunit of a nucleic acid consisting of a phosphate group, a 5-carbon sugar, and a nitrogenous base (also referred to herein as "nucleobase"). The 5-carbon sugar found in RNA is ribose. In DNA, the 5-carbon sugar is 2'-deoxyribose. The term also includes analogs of such subunits, such as a methoxy group at the 2' position of the ribose (also referred to herein as "2'-O-Me" or "2'-methoxy").

By "RNA and DNA equivalents" is meant RNA and DNA molecules having essentially the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence. By "DNA/RNA chimeric" is meant a nucleic acid comprising both DNA and RNA nucleotides. Unless the context clearly dictates otherwise, reference to a GBS nucleic acid includes GBS RNA and DNA equivalents and DNA/RNA chimerics thereof.

A "target nucleic acid" as used herein is a nucleic acid comprising a target sequence to be amplified. Target nucleic acids may be DNA or RNA, and may be either single-stranded or double-stranded. The target nucleic acid may include other sequences besides the target sequence, which may not be amplified.

The term "target sequence" as used herein refers to the particular nucleotide sequence of the target nucleic acid that is to be amplified and/or detected. The "target sequence" includes the complexing sequences to which oligonucleotides (e.g., priming oligonucleotides and/or promoter oligonucleotides) complex during an amplification processes (e.g., PCR, TMA). Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands.

"Target-hybridizing sequence" or "target-specific sequence" is used herein to refer to the portion of an oligomer that is configured to hybridize with a target nucleic acid sequence. Preferably, the target-hybridizing sequences are configured to specifically hybridize with a target nucleic acid sequence. Target-hybridizing sequences may be 100% complementary to the portion of the target sequence to which they are configured to hybridize, but not necessarily. Target-hybridizing sequences may also include inserted, deleted and/or substituted nucleotide residues relative to a target sequence. Less than 100% complementarity of a target-hybridizing sequence to a target sequence may arise, for example, when the target nucleic acid is a plurality strains within a species, such as would be the case for an oligomer configured to hybridize to various serotypes of GBS. It is understood that other reasons exist for configuring a target-hybridizing sequence to have less than 100% complementarity to a target nucleic acid.

The term "target a sequence," as used herein in reference to a region of GBS nucleic acid, refers to a process whereby an oligonucleotide hybridizes to a target sequence in a manner that allows for amplification and detection as described herein. In one preferred embodiment, the oligonucleotide is complementary with the targeted GBS nucleic acid sequence and contains no mismatches. In another preferred embodiment, the oligonucleotide is complementary but contains 1, 2, 3, 4, or 5 mismatches with the targeted GBS nucleic acid sequence. Preferably, the oligomer specifically hybridizes to the target sequence.

The term "configured to" denotes an actual arrangement of the polynucleotide sequence configuration of a referenced oligonucleotide target-hybridizing sequence. For example, amplification oligomers that are configured to generate a specified amplicon from a target sequence have polynucleotide sequences that hybridize to the target sequence and can be used in an amplification reaction to generate the amplicon. Also as an example, oligonucleotides that are configured to specifically hybridize to a target sequence have a polynucleotide sequence that specifically hybridizes to the referenced sequence under stringent hybridization conditions.

The term "configured to specifically hybridize to" as used herein means that the target-hybridizing region of an amplification oligonucleotide, detection probe, or other oligonucleotide is designed to have a polynucleotide sequence that could target a sequence of the referenced GBS target region. Such an oligonucleotide is not limited to targeting that sequence only, but is rather useful as a composition, in a kit, or in a method for targeting a GBS target nucleic acid. The oligonucleotide is designed to function as a component of an assay for amplification and detection of GBS from a sample, and therefore is designed to target GBS in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that an accurate detection of target nucleic acid in a sample can be determined.

The term "region," as used herein, refers to a portion of a nucleic acid wherein said portion is smaller than the entire nucleic acid. For example, when the nucleic acid in reference is an oligonucleotide promoter primer, the term "region" may be used refer to the smaller promoter portion. Similarly, and also as example only, when the nucleic acid is a GBS target nucleic acid, the term "region" may be used to refer to a smaller area of the nucleic acid, wherein the smaller area is targeted by one or more oligonucleotides of the present disclosure. As another non-limiting example, when the nucleic acid in reference is an amplicon, the term region may be used to refer to the smaller nucleotide sequence identified for hybridization by the target-hybridizing sequence of a probe.

"Oligomer," "oligonucleotide," or "oligo" refers to a nucleic acid of generally less than 1,000 nucleotides (nt), including those in a size range having a lower limit of about 2 to 5 nt and an upper limit of about 500 to 900 nt. Some particular embodiments are oligomers in a size range with a lower limit of about 5 to 15, 16, 17, 18, 19, or 20 nt and an upper limit of about 50 to 600 nt, and other particular embodiments are in a size range with a lower limit of about 10 to 20 nt and an upper limit of about 22 to 100 nt. Oligomers may be purified from naturally occurring sources, but may be synthesized by using any well-known enzymatic or chemical method. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase; it may function as a primer and provide a promoter if it contains a sequence recognized by an RNA polymerase and allows for transcription (e.g., a T7 Primer); and it may function to detect a target nucleic acid if it is capable of hybridizing to the target nucleic acid, or an amplicon thereof, and further provides a detectible moiety (e.g., an acridinium-ester compound). Oligomers may be referred to by a functional name (e.g., capture probe, primer or promoter primer) but those skilled in the art will understand that such terms refer to oligomers.

As used herein, an oligonucleotide "substantially corresponding to" a specified reference nucleic acid sequence means that the oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from a reference sequence and still hybridize to the same target nucleic acid sequence. It is also understood that a first nucleic acid corresponding to a second nucleic acid includes the RNA or DNA equivalent thereof as well as DNA/RNA chimerics thereof, and includes the complements thereof, unless the context clearly dictates otherwise. This variation from the nucleic acid may be stated in terms of a percentage of identical bases within the sequence or the percentage of perfectly complementary bases between the probe or primer and its target sequence; thus, in certain embodiments, an oligonucleotide "substantially corresponds" to a reference nucleic acid sequence if these percentages of base identity or complementarity are from 100% to about 80%, preferably from 100% to about 85%, or more preferably from 100% to about 90% or from 100% to about 95%. This variation from the nucleic acid may also be stated in terms of the number of nucleobase substitutions in a nucleic acid sequence relative to a reference sequence, or the number of mismatches within a sequence relative to a target sequence; thus, in certain embodiments, an oligonucleotide "substantially corresponds" to a reference nucleic acid sequence if this number of nucleobase substitutions or mismatches is up to four, preferable up to three, or more preferably up to two or up to one substitution(s) or mismatch(es) (i.e., from zero to four, preferably from zero to three, or more preferably from zero to two or from zero to one, inclusive). Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

As used herein, the phrase "or its complement, or an RNA equivalent or DNA/RNA chimeric thereof," with reference to a DNA sequence, includes (in addition to the referenced DNA sequence) the complement of the DNA sequence, an RNA equivalent of the referenced DNA sequence, an RNA equivalent of the complement of the referenced DNA sequence, a DNA/RNA chimeric of the referenced DNA sequence, and a DNA/RNA chimeric of the complement of the referenced DNA sequence. Similarly, the phrase "or its complement, or a DNA equivalent or DNA/RNA chimeric thereof," with reference to an RNA sequence, includes (in addition to the referenced RNA sequence) the complement of the RNA sequence, a DNA equivalent of the referenced RNA sequence, a DNA equivalent of the complement of the referenced RNA sequence, a DNA/RNA chimeric of the referenced RNA sequence, and a DNA/RNA chimeric of the complement of the referenced RNA sequence.

An "amplification oligonucleotide" or "amplification oligomer" is an oligonucleotide that hybridizes to a target nucleic acid, or its complement, and participates in a nucleic acid amplification reaction, e.g., serving as a primer or and promoter-primer. Particular amplification oligomers contain at least about 10 contiguous bases, and optionally at least 11, 12, 13, 14, 15, 16, 17, 18, 19, or 20 contiguous bases, that are complementary to a region of the target nucleic acid sequence or its complementary strand. The contiguous bases may be at least about 80%, at least about 90%, or completely complementary to the target sequence to which the amplification oligomer binds. One skilled in the art will understand that the recited ranges include all whole and rational numbers within the range (e.g., 92% or 98.377%). Particular amplification oligomers are about 10 to about 60 bases long and optionally may include modified nucleotides.

A "primer" is an oligomer that hybridizes to a template nucleic acid and has a 3' end that is extended by polymerization. A primer may be optionally modified, e.g., by including a 5' region that is non-complementary to the target sequence. Such modification can include functional additions, such as tags, promoters, or other non-target-specific sequences used or useful for manipulating or amplifying the primer or target oligonucleotide.

Within the context of transcription-mediated amplification, a primer modified with a 5' promoter sequence is referred to herein as a "promoter-primer." A person of ordinary skill in the art of molecular biology or biochemistry will understand that an oligomer that can function as a primer can be modified to include a 5' promoter sequence and then function as a promoter-primer, and, similarly, any promoter-primer can serve as a primer with or without its 5' promoter sequence. A promoter-primer modified to incorporate a 3' blocked end is referred to herein as a "promoter provider," which is capable of hybridizing to a target nucleic acid and providing an upstream promoter sequence that serves to initiate transcription, but does not provide a primer for oligo extension.

"Non-target-specific sequence" or "non-target-hybridizing sequence" as used herein refers to a region of an oligomer sequence, wherein said region does not stably hybridize with a target sequence under standard hybridization conditions. Oligomers with non-target-specific sequences include, but are not limited to, promoter primers and molecular beacons.

"Nucleic acid amplification" refers to any in vitro procedure that produces multiple copies of a target nucleic acid sequence, or its complementary sequence, or fragments thereof (i.e., an amplified sequence containing less than the complete target nucleic acid). Examples of nucleic acid amplification procedures include transcription associated methods, such as transcription-mediated amplification (TMA), nucleic acid sequence-based amplification (NASBA) and others (e.g., U.S. Pat. Nos. 5,399,491, 5,554, 516, 5,437,990, 5,130,238, 4,868,105, and 5,124,246), replicase-mediated amplification (e.g., U.S. Pat. No. 4,786, 600), the polymerase chain reaction (PCR) (e.g., U.S. Pat. Nos. 4,683,195, 4,683,202, and 4,800,159), ligase chain reaction (LCR) (e.g., EP Patent No. 0320308), helicase-dependent amplification (e.g., U.S. Pat. No. 7,282,328), and strand-displacement amplification (SDA) (e.g., U.S. Pat. No. 5,422,252). Amplification may be linear or exponential. Replicase-mediated amplification uses self-replicating RNA molecules, and a replicase such as QB-replicase. PCR amplification uses DNA polymerase, primers, and thermal cycling steps to synthesize multiple copies of the two complementary strands of DNA or cDNA. LCR amplification uses at least four separate oligonucleotides to amplify a target and its complementary strand by using multiple cycles of hybridization, ligation, and denaturation. Helicase-dependent amplification uses a helicase to separate the two strands of a DNA duplex generating single-stranded templates, followed by hybridization of sequence-specific primers hybridize to the templates and extension by DNA polymerase to amplify the target sequence. SDA uses a primer that contains a recognition site for a restriction endonuclease that will nick one strand of a hemimodified DNA duplex that includes the target sequence, followed by amplification in a series of primer extension and strand displacement steps. Particular embodiments use PCR or TMA, but it will be apparent to persons of ordinary skill in the art that oligomers disclosed herein may be readily used as primers in other amplification methods.

Transcription associated amplification uses a DNA polymerase, an RNA polymerase, deoxyribonucleoside triphosphates, ribonucleoside triphosphates, a promoter-containing oligonucleotide, and optionally may include other oligonucleotides, to ultimately produce multiple RNA transcripts from a nucleic acid template (described in detail in, e.g., U.S. Pat. Nos. 5,399,491 and 5,554,516 to Kacian et al.; U.S. Pat. No. 5,437,990 to Burg et al.; PCT Publication Nos. WO 88/01302 and WO 88/10315 (Gingeras et al.); U.S. Pat. No. 5,130,238 to Malek et al.; U.S. Pat. Nos. 4,868,105 and 5,124,246 to Urdea et al.; PCT Publication No. WO 94/03472 (McDonough et al.); and PCT Publication No. WO 95/03430 (Ryder et al.)). Methods that use TMA are described in detail previously (e.g., U.S. Pat. Nos. 5,399,491 and 5,554,516).

In cyclic amplification methods that detect amplicons in real-time, the term "Threshold cycle" (Ct) is a measure of the emergence time of a signal associated with amplification of target, and is generally 10× standard deviation of the normalized reporter signal. Once an amplification reaches the "threshold cycle," generally there is considered to be a positive amplification product of a sequence to which the probe binds. The identity of the amplification product can then be determined through methods known to one of skill in the art, such as gel electrophoresis, nucleic acid sequencing, and other such analytical procedures.

By "amplicon" or "amplification product" is meant a nucleic acid molecule generated in a nucleic acid amplification reaction and which is derived from a target nucleic acid. An amplicon or amplification product contains a target nucleic acid sequence that may be of the same or opposite sense as the target nucleic acid.

As used herein, the term "relative fluorescence unit" ("RFU") is a unit of measurement of fluorescence intensity. RFU varies with the characteristics of the detection means used for the measurement, and can be used as a measurement to compare relative intensities between samples and controls.

"Detection probe oligomer," "detection probe," or "probe" refers to an oligomer that hybridizes specifically to a target sequence, including an amplified sequence, under conditions that promote nucleic acid hybridization, for detection of the target nucleic acid. Detection may either be direct (i.e., probe hybridized directly to the target) or indirect (i.e., a probe hybridized to an intermediate structure that links the probe to the target). Detection probes may be DNA, RNA, analogs thereof or combinations thereof (e.g., DNA/RNA chimerics), and they may be labeled or unlabeled. Detection probes may further include alternative backbone linkages such as, e.g., 2'-O-methyl linkages. A probe's target sequence generally refers to the specific sequence within a larger sequence which the probe hybridizes specifically. A detection probe may include target-specific sequence(s) and non-target-specific sequence(s). Such non-target-specific sequences can include sequences which will confer a desired secondary or tertiary structure, such as a hairpin structure, which can be used to facilitate detection and/or amplification (see, e.g., U.S. Pat. Nos. 5,118,801, 5,312,728, 6,835,542, and 6,849,412). Probes of a defined sequence may be produced by techniques known to those of ordinary skill in the art, such as by chemical synthesis, and by in vitro or in vivo expression from recombinant nucleic acid molecules.

By "hybridization" or "hybridize" is meant the ability of two completely or partially complementary nucleic acid strands to come together under specified hybridization assay conditions in a parallel or antiparallel orientation to form a stable structure having a double-stranded region. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art. See, e.g., R. L. P. Adams et al., *The Biochemistry of the Nucleic Acids* (11th ed. 1992).

By "preferentially hybridize" is meant that under stringent hybridization conditions, an amplification or detection probe oligomer can hybridize to its target nucleic acid to form stable oligomer:target hybrid, but not form a sufficient number of stable oligomer:non-target hybrids. Amplification and detection oligomers that preferentially hybridize to a target nucleic acid are useful to amplify and detect target nucleic acids, but not non-targeted organisms, especially phylogenetically closely related organisms. Thus, the oligomer hybridizes to target nucleic acid to a sufficiently greater extent than to non-target nucleic acid to enable one having ordinary skill in the art to accurately amplify and/or detect the presence (or absence) of nucleic acid derived from the specified target as appropriate. In general, reducing the degree of complementarity between an oligonucleotide sequence and its target sequence will decrease the degree or rate of hybridization of the oligonucleotide to its target region. However, the inclusion of one or more non-complementary nucleosides or nucleobases may facilitate the ability of an oligonucleotide to discriminate against non-target organisms.

Preferential hybridization can be measured using techniques known in the art and described herein, such as in the examples provided below. In some embodiments, there is at least a 10-fold difference between target and non-target hybridization signals in a test sample, at least a 100-fold difference, or at least a 1,000-fold difference. In some embodiments, non-target hybridization signals in a test sample are no more than the background signal level.

By "stringent hybridization conditions," or "stringent conditions" is meant conditions permitting an oligomer to preferentially hybridize to a target nucleic acid and not to nucleic acid derived from a closely related non-target nucleic acid. While the definition of stringent hybridization conditions does not vary, the actual reaction environment that can be used for stringent hybridization may vary depending upon factors including the GC content and length of the oligomer, the degree of similarity between the oligomer sequence and sequences of non-target nucleic acids that may be present in the test sample, and the target sequence. Hybridization conditions include the temperature and the composition of the hybridization reagents or solutions. Exemplary hybridization assay conditions for amplifying and/or detecting target nucleic acids derived from one or more serotypes of GBS with the oligomers of the present disclosure correspond to a temperature of about 60° C. when the salt concentration, such as a monovalent salt, e.g., KCl, is in the range of about 0.6-0.9 M. Other acceptable stringent hybridization conditions are readily ascertained by those having ordinary skill in the art.

By "assay conditions" is meant conditions permitting stable hybridization of an oligonucleotide to a target nucleic acid. Assay conditions do not require preferential hybridization of the oligonucleotide to the target nucleic acid.

"Label" or "detectable label" refers to a moiety or compound joined directly or indirectly to a probe that is detected or leads to a detectable signal. Direct joining may use covalent bonds or non-covalent interactions (e.g., hydrogen bonding, hydrophobic or ionic interactions, and chelate or coordination complex formation) whereas indirect joining may use a bridging moiety or linker (e.g., via an antibody or additional oligonucleotide(s), which amplify a detectable signal. Any detectable moiety may be used, e.g., radionuclide, ligand such as biotin or avidin, enzyme, enzyme substrate, reactive group, chromophore such as a dye or particle (e.g., latex or metal bead) that imparts a detectable color, luminescent compound (e.g., bioluminescent, phosphorescent, or chemiluminescent compound), and fluorescent compound (i.e., fluorophore). Embodiments of fluorophores include those that absorb light in the range of about 495 to 650 nm and emit light in the range of about 520 to 670 nm, which include those known as FAM™, TET™, CAL FLUOR™ (Orange or Red), and QUASAR™ compounds. Fluorophores may be used in combination with a quencher molecule that absorbs light when in close proximity to the fluorophore to diminish background fluorescence. Such quenchers are well known in the art and include, e.g., BLACK HOLE QUENCHER™ (or BHQ™) or TAMRA™ compounds. Particular embodiments include a "homogeneous detectable label" that is detectable in a homogeneous system in which bound labeled probe in a mixture exhibits a detectable change compared to unbound labeled probe, which allows the label to be detected without physically removing hybridized from unhybridized labeled probe (e.g., U.S. Pat. Nos. 5,283,174, 5,656,207, and 5,658,737). Particular homogeneous detectable labels include chemiluminescent compounds, including acridinium ester ("AE") compounds, such as standard AE or AE derivatives which are well known (U.S. Pat. Nos. 5,656,207, 5,658,737, and 5,639,604). Methods of synthesizing labels, attaching labels to nucleic acid, and detecting signals from labels are well known (e.g., Sambrook et al., *Molecular Cloning, A Laboratory Manual*, 2nd ed. (Cold Spring Harbor Laboratory Press, Cold Spring Harbor, N.Y., 1989) at Chapt. 10, and U.S. Pat. Nos. 5,658,737, 5,656,207, 5,547,842, 5,283,174, and 4,581,333, and EP Pat. App. 0 747 706). Particular methods of linking an AE compound to a nucleic acid are known (e.g., U.S. Pat. Nos. 5,585,481 and 5,639,604, see column 10, line 6 to column 11, line 3, and Example 8). Particular AE labeling positions are a probe's central region and near a region of A/T base pairs, at a probe's 3' or 5' terminus, or at or near a mismatch site with a known sequence that is the probe should not detect compared to the desired target sequence. Other detectably labeled probes include TaqMan™ probes, molecular torches, and molecular beacons. TaqMan™ probes include a donor and acceptor label wherein fluorescence is detected upon enzymatically degrading the probe during amplification in order to release the fluorophore from the presence of the quencher. Molecular torches and beacons exist in open and closed configurations wherein the closed configuration quenches the fluorophore and the open position separates the fluorophore from the quencher to allow fluorescence. Hybridization to target opens the otherwise closed probes.

Sequences are "sufficiently complementary" if they allow stable hybridization of two nucleic acid sequences, e.g., stable hybrids of probe and target sequences, although the sequences need not be completely complementary. That is, a "sufficiently complementary" sequence that hybridizes to another sequence by hydrogen bonding between a subset series of complementary nucleotides by using standard base pairing (e.g., G:C, A:T, or A:U), although the two sequences may contain one or more residues (including abasic positions) that are not complementary so long as the entire sequences in appropriate hybridization conditions to form a stable hybridization complex. Sufficiently complementary sequences may be at least about 80%, at least about 90%, or completely complementary in the sequences that hybridize together. Appropriate hybridization conditions are well-known to those skilled in the art, can be predicted based on sequence composition, or can be determined empirically by using routine testing (e.g., Sambrook et al., *Molecular Cloning, A Laboratory Manual*, $2^{nd}$ ed. at §§ 1.90-1.91, 7.37-7.57, 9.47-9.51 and 11.47-11.57, particularly §§ 9.50-9.51, 11.12-11.13, 11.45-11.47 and 11.55-11.57).

A "non-extendable" oligomer includes a blocking moiety at or near its 3'-terminus to prevent extension. A blocking group near the 3' end is in some embodiments within five residues of the 3' end and is sufficiently large to limit binding of a polymerase to the oligomer, and other embodiments contain a blocking group covalently attached to the 3' terminus. Many different chemical groups may be used to block the 3' end, e.g., alkyl groups, non-nucleotide linkers, alkane-diol dideoxynucleotide residues, and cordycepin. Further examples of blocking moieties include a 3'-deoxy nucleotide (e.g., a 2',3'-dideoxy nucleotide); a 3'-phosphorylated nucleotide; a fluorophore, quencher, or other label that interferes with extension; an inverted nucleotide (e.g., linked to the preceding nucleotide through a 3'-to-3' phosphodiester, optionally with an exposed 5'-OH or phosphate); or a protein or peptide joined to the oligonucleotide so as to prevent further extension of a nascent nucleic acid chain by a polymerase. A non-extendable oligonucleotide of the present disclosure may be at least 10 bases in length, and may be up to 15, 20, 25, 30, 35, 40, 50 or more nucleotides in length. Non-extendable oligonucleotides that comprise a detectable label can be used as probes.

References, particularly in the claims, to "the sequence of SEQ ID NO: X" refer to the base sequence of the corresponding sequence listing entry and do not require identity of the backbone (e.g., RNA, 2'-O-Me RNA, or DNA) or base modifications (e.g., methylation of cytosine residues) unless the context clearly dictates otherwise.

"Sample preparation" refers to any steps or method that treats a sample for subsequent amplification and/or detection of GBS nucleic acids present in the sample. Samples may be complex mixtures of components of which the target nucleic acid is a minority component. Sample preparation may include any known method of concentrating components, such as microbes or nucleic acids, from a larger sample volume, such as by filtration of airborne or waterborne particles from a larger volume sample or by isolation of microbes from a sample by using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically capture a target nucleic acid and separate it from other sample components (e.g., as described in U.S. Pat. No. 6,110,678 and International Patent Application Pub. No. WO 2008/016988, each incorporated by reference herein).

"Separating" or "purifying" means that one or more components of a sample are removed or separated from other sample components. Sample components include target nucleic acids usually in a generally aqueous solution phase, which may also include cellular fragments, proteins, carbohydrates, lipids, and other nucleic acids. "Separating" or "purifying" does not connote any degree of purification. Typically, separating or purifying removes at least 70%, or at least 80%, or at least 95% of the target nucleic acid from other sample components.

The term "non-linear surfactant," as used herein, means a surfactant having a branched chain structure. A non-linear surfactant may include one or more ring structures, which may be, for example, in a principal chain and/or in one or more branch chains. Exemplary non-linear surfactants include polysorbate 20, polysorbate 40, polysorbate 60, and digitonin. In certain variations, a non-linear surfactant is non-ionic.

The term "specificity," in the context of an amplification and/or detection system, is used herein to refer to the characteristic of the system which describes its ability to distinguish between target and non-target sequences dependent on sequence and assay conditions. In terms of nucleic acid amplification, specificity generally refers to the ratio of the number of specific amplicons produced to the number of side-products (e.g., the signal-to-noise ratio). In terms of detection, specificity generally refers to the ratio of signal produced from target nucleic acids to signal produced from non-target nucleic acids.

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, e.g., the ratio of specific amplicons to side-products.

DETAILED DESCRIPTION OF THE INVENTION

The present invention provides compositions, kits, and methods for amplifying and detecting Group B *Streptococcus* (GBS; *Streptococcus agalactiae*) nucleic acid from a sample. Preferably, the samples are biological samples. The compositions, kits, and methods provide oligonucleotide sequences that recognize target sequences of the GBS genome, including target sequences of GBS serotypes Ia, Ib, Ic, II, III, IV, V, VI, VII, VIII, and IX, or their complementary sequences. Such oligonucleotides may be used as amplification oligonucleotides, which may include primers, promoter primers, blocked oligonucleotides, and promoter provider oligonucleotides, whose functions have been described previously (see, e.g., U.S. Pat. Nos. 4,683,195; 4,683,202; 4,800,159; 5,399,491; 5,554,516; 5,824,518; and 7,374,885; each incorporated by reference herein). Other oligonucleotides may be used as probes for detecting amplified sequences of GBS, or for capture of GBS target nucleic acid.

The methods provide for the sensitive and specific detection of GBS nucleic acids. The methods include performing a nucleic acid amplification of an GBS target region and detecting the amplified product by, for example, specifically hybridizing the amplified product with a nucleic acid detection probe that provides a signal to indicate the presence of GBS in the sample. The amplification step includes contacting the sample with one or more amplification oligomers specific for a target sequence in a GBS target nucleic acid to produce an amplified product if GBS nucleic acid is present in the sample. Amplification synthesizes additional copies of the target sequence or its complement by using at least one nucleic acid polymerase and an amplification oligomer to produce the copies from a template strand (e.g., by extending the sequence from a primer using the template strand). One embodiment for detecting the amplified product uses a hybridizing step that includes contacting the amplified product with at least one detection probe oligomer specific for a sequence amplified by the selected amplification oligomers, e.g., a sequence contained in the target sequence flanked by a pair of selected amplification oligomers.

Preferred compositions of the instant invention are configured to specifically hybridize to nucleic acid of all GBS serotypes Ia, Ib, Ic, II, III, IV, V, VI, VII, VIII, and IX with minimal cross-reactivity to other, non-GBS nucleic acids suspected of being in a sample (e.g., other bacterial pathogens). In certain variations, compositions of the invention further allow detection of sequences on a non-hemolytic strain of GBS. In some aspects, the compositions of the instant invention are configured to specifically hybridize to GBS nucleic acid with minimal cross-reactivity to one or more non-GBS pathogens listed in any of Tables 9-11, 15, 16, 20, and 22 (see Examples, infra). In one aspect, the compositions of the instant invention are part of a multiplex system that further includes components and methods for detecting one of more of these non-GBS pathogens.

In certain aspects of the invention, a composition comprising at least two amplification oligomers is provided for determining the presence or absence of GBS in a sample. Typically, the composition includes at least two amplification oligomers for amplifying a target region of a GBS target nucleic acid corresponding to the sequence of SEQ ID NO:1 (SIP gene) or SEQ ID NO:2 (CFB gene). In such embodiments, at least one amplification oligomer comprises a target-hybridizing sequence in the sense orientation ("sense THS") and at least one amplification oligomer comprises a target-hybridizing sequence in the antisense orientation ("antisense THS"), where the sense THS and antisense THS are each configured to specifically hybridize to a GBS target sequence corresponding to a sequence contained within SEQ ID NO:1 or SEQ ID NO:2 and where the target-hybridizing sequences are selected such that the GBS sequence targeted by antisense THS is situated downstream of the GBS sequence targeted by the sense THS (i.e., the at least two amplification oligomers are situated such that they flank the target region to be amplified).

In some variations, a composition includes (i) a SIP-specific amplification oligomer comprising a SIP-specific target-hybridizing sequence substantially corresponding to, or identical to, the sequence shown in SEQ ID NO:3, SEQ ID NO:4, SEQ ID NO:7, or SEQ ID NO:8, or the complement thereof or an RNA equivalent or DNA/RNA chimeric thereof. In some variations, a composition includes (ii) a CFB-specific amplification oligomer comprising a CFB-specific target-hybridizing sequence that is from about 17 to about 24 contiguous nucleotides and substantially corresponding to, or identical to, a sequence that is contained in the sequence of SEQ ID NO:26, or the complement thereof or an RNA equivalent or DNA/RNA chimeric thereof; in some such embodiments, the CFB-specific target-hybridizing sequence includes a sequence that substantially corresponds to, or is identical to, the sequence of SEQ ID NO:28 or SEQ ID NO:27, or the complement thereof or an RNA equivalent or DNA/RNA chimeric thereof (e.g., a sequence substantially corresponding to, or identical to, the sequence shown in SEQ ID NO:12 or SEQ ID NO:14, or the complement thereof or an RNA equivalent or DNA/RNA chimeric thereof), or is a sequence substantially corresponding to, or identical to, the sequence shown in SEQ ID NO:18, or the complement thereof or an RNA equivalent or DNA/RNA chimeric thereof. In some variations, a composition includes (iii) a CFB-specific amplification oligomer comprising a CFB-specific target-hybridizing sequence substantially corresponding to, or identical to, the sequence shown in SEQ ID NO:13, SEQ ID NO:15, SEQ ID NO:16, SEQ ID NO:17, SEQ ID NO:20, or SEQ ID NO:21, or the complement thereof or an RNA equivalent or DNA/RNA chimeric thereof. In variations comprising a SIP-specific or CFB-specific amplification oligomer of (i), (ii), or (iii) as above, the oligomer combination includes at least one an amplification oligomer comprising an SIP-specific or CFB-specific target-hybridizing sequence of the opposite polarity (sense vs. antisense or vice versa) as the target-hybridizing sequence of the oligomer of (i), (ii), or (iii), such that at least two amplification oligomers flank a target region to be amplified. In certain embodiments, the composition is provided as an aqueous or dried formulation for amplification of GBS nucleic acid, or a reaction mixture comprising or reconstituted from such a formulation.

In more specific embodiments of the present invention, a composition for determining the presence or absence of GBS in a sample includes (1) at least one amplification oligomer comprising a SIP-specific or CFB-specific target-hybridizing region substantially corresponding to at least one sense oligomer sequence depicted in Table 1 below, and (2) at least one amplification oligomer comprising a SIP-specific or CFB-specific target hybridizing region substantially corresponding to at least one antisense oligomer sequence depicted in Table 1. In some such embodiments, the composition includes a first SIP-specific amplification oligomer and a first CFB-specific amplification oligomer of (1) above and a second SIP-specific and second CFB-specific amplification oligomer of (2) above. In particular variations, the sense and/or antisense target-hybridizing sequence(s) of an amplification oligomer combination comprises or consists of the sense and/or antisense sequence(s) selected from Table 1.

TABLE 1

Exemplary Sense and Antisense Amplification Oligomer Target-hybridizing Sequences for Amplification of GBS SIP or CFB Target Regions

| SEQ ID NO: | Sequence (5' → 3') | Sense/ Antisense[1] | Target Gene |
|---|---|---|---|
| 3 | CAGTCGCAAGTGTTCAAGC | Sense | SIP |
| 4 | AACGCTTAGTGTATCACCATAT | Antisense | SIP |
| 7 | AACAAATGCTGCTGGTCAAA | Sense | SIP |
| 8 | AGAATATGTCTTCATTGGCGAA | Antisense | SIP |
| 12 | GTGGCTGGTGCATTGTTATTT | Sense | CFB |
| 13 | CCATTTGCTGGGCTTGATTATT | Antisense | CFB |
| 14 | TAGTGGCTGGTGCATTGTT | Sense | CFB |
| 15 | CATTTGCTGGGCTTGATTATTACT | Antisense | CFB |
| 16 | CTGGAATACACGCTTTACTAGAGATA | Sense | CFB |
| 17 | ACTTGTTGTACCGTAACATTTGG | Antisense | CFB |
| 18 | TATCTATCTGGAACTCTAGTGGCT | Sense | CFB |
| 20 | CAAAGATAATGTTCAGGGAACAGA | Sense | CFB |
| 21 | GCTTCTACACGACTACCAATAGA | Antisense | CFB |

[1]The Sense/Antisense designation of these sequences is for exemplary purposes only. Such designation does not necessarily limit a sequence to the accompanying designation.

In certain variations, a composition for determining the presence or absence of GBS in a sample as described herein further comprises at least one detection probe oligomer configured to specifically hybridize to a GBS SIP or CFB target sequence that is amplifiable using the first and second amplification oligomers (e.g., an SIP or CFB target sequence contained within SEQ ID NO:1 or SEQ ID NO:2, or the complement thereof, that is flanked by the target-hybridizing sequences of the first and second amplification oligomers). Particularly suitable SIP-specific detection probe oligomers include, for example, oligomers comprising a SIP-specific target-hybridizing sequence substantially corresponding to, or identical to, the sequence shown in SEQ ID NO:9 or SEQ ID NO:11, or the complement thereof or an RNA equivalent or DNA/RNA chimeric thereof. Particularly suitable CFB-specific detection probe oligomers include, for example, oligomers comprising a CFB-specific target-hybridizing sequence substantially corresponding to, or identical to, the sequence shown in SEQ ID NO:22, SEQ ID NO:23, SEQ ID NO:24, or SEQ ID NO:25, or the complement thereof or an RNA equivalent or DNA/RNA chimeric thereof. A detection probe oligomer may contain a 2'-methoxy backbone at one or more linkages in the nucleic acid backbone. In some variations, a composition includes at least two detection probe oligomers. In certain embodiments, a detection probe oligomer is provided in an aqueous or dried formulation for detection of GBS nucleic acid, or a reaction mixture comprising or reconstituted from such a formulation Typically, a detection probe oligomer in accordance with the present invention further includes a label. Particularly suitable labels include compounds that emit a detectable light signal, e.g., fluorophores or luminescent (e.g., chemiluminescent) compounds that can be detected in a homogeneous mixture. More than one label, and more than one type of label, may be present on a particular probe, or detection may rely on using a mixture of probes in which each probe is labeled with a compound that produces a detectable signal (see, e.g., U.S. Pat. Nos. 6,180,340 and 6,350,579, each incorporated by reference herein). Labels may be attached to a probe by various means including covalent linkages, chelation, and ionic interactions, but preferably the label is covalently attached. For example, in some embodiments, a detection probe has an attached chemiluminescent label such as, e.g., an acridinium ester (AE) compound (see, e.g., U.S. Pat. Nos. 5,185,439; 5,639,604; 5,585,481; and 5,656,744; each incorporated by reference herein). A label, such as, e.g., a fluorescent or chemiluminescent label, is typically attached to the probe by a non-nucleotide linker (see, e.g., U.S. Pat. Nos. 5,585,481; 5,656,744; and 5,639,604, particularly at column 10, line 6 to column 11, line 3, and Example 8; each incorporated by reference herein).

In some embodiments, a probe (e.g., comprising a fluorescent label) further includes a second label that interacts with the first label. For example, the second label can be a quencher. Detection probes comprising both a fluorescent label and a quencher, a combination are particularly useful in fluorescence resonance energy transfer (FRET) assays. Specific variations of such detection probes include, e.g., a TaqMan™ detection probe (Roche Molecular Diagnostics) and a "molecular beacon" (see, e.g., Tyagi et al., *Nature Biotechnol.* 16:49-53, 1998; U.S. Pat. Nos. 5,118,801 and 5,312,728; each incorporated by reference herein). TaqMan™ probes (or similar dual-labeled linear probes comprising both a fluorescent label and a quencher), can be used in assays where hybridization of the probe to a target or amplicon followed by nucleolysis by a polymerase comprising 5'-3' exonuclease activity results in liberation of the fluorescent label and thereby increased fluorescence, or fluorescence independent of the interaction with the second label.

In some applications, a detection probe exhibiting at least some degree of self-complementarity are used to facilitate detection of probe:target duplexes in a test sample without first requiring the removal of unhybridized probe prior to detection. Specific embodiments of such detection probes include, for example, probes that form conformations held by intramolecular hybridization, such as conformations generally referred to as hairpins. Suitable hairpin probes include a "molecular torch" (see, e.g., U.S. Pat. Nos. 6,849,412; 6,835,542; 6,534,274; and 6,361,945) and a "molecular beacon" (see, e.g., U.S. Pat. Nos. 5,118,801 and 5,312,728). Molecular torches include distinct regions of self-complementarity (coined "the target binding domain" and "the target closing domain") which are connected by a joining region (e.g., a —($CH_2CH_2O)_3$— linker) and which hybridize to one another under predetermined hybridization assay conditions. When exposed to an appropriate target or denaturing conditions, the two complementary regions (which may be fully or partially complementary) of the molecular torch melt, leaving the target binding domain available for hybridization to a target sequence when the predetermined hybridization assay conditions are restored. Molecular torches are designed so that the target binding domain favors hybridization to the target sequence over the target closing domain. The target binding domain and the target closing domain of a molecular torch include interacting labels (e.g., fluorescent/quencher) positioned so that a different signal is produced when the molecular torch is self-hybridized as opposed to when the molecular torch is hybridized to a target nucleic acid, thereby permitting detection of probe:target duplexes in a test sample in the presence of unhybridized probe having a viable label associated therewith.

In other embodiments, a detection probe is a linear oligomer that does not substantially form conformations held by intramolecular bonds. In specific variations, a linear detection probe oligomer includes a chemiluminescent compound as the label (e.g., an acridinium ester (AE) compound). In other embodiments, a linear detection probe oligomer includes a fluorophore as the label. In some embodiments of a linear detection probe oligomer comprising a fluorophore, the oligomer further includes a quenching moiety (e.g., a TaqMan probe).

Examples of interacting donor/acceptor label pairs that may be used in connection with the disclosure, making no attempt to distinguish FRET from non-FRET pairs, include fluorescein/tetramethylrhodamine, IAEDANS/fluororescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, Texas Red/DABCYL, CY5/BH1, CY5/BH2, CY3/BH1, CY3/BH2 and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. Non-fluorescent acceptors such as DABCYL and the QSY7 dyes advantageously eliminate the potential problem of background fluorescence resulting from direct (i.e., non-sensitized) acceptor excitation. Exemplary fluorophore moieties that can be used as one member of a donor-acceptor pair include fluorescein, ROX, and the CY dyes (such as CY5). Exemplary quencher moieties that can be used as another member of a donor-acceptor pair include DABCYL and the BLACK HOLE QUENCHER moieties which are available from Biosearch Technologies, Inc., (Novato, Calif.).

In some embodiments, a labeled oligomer (e.g., a detection probe) is non-extendable. For example, the labeled oligomer can be rendered non-extendable by 3'-phosphorylation, having a 3'-terminal 3'-deoxynucleotide (e.g., a terminal 2',3'-dideoxynucleotide), having a 3'-terminal inverted nucleotide (e.g., in which the last nucleotide is inverted such that it is joined to the penultimate nucleotide by a 3' to 3' phosphodiester linkage or analog thereof, such as a phosphorothioate), or having an attached fluorophore, quencher, or other label that interferes with extension (possibly but not necessarily attached via the 3' position of the terminal nucleotide). In some embodiments, the 3'-terminal nucleotide is not methylated.

Also provided by the present invention are compositions comprising one or more detection probe oligomers as described herein.

In some aspects, the present invention provides methods utilizing an oligomer or oligomer combination as described herein. Any method disclosed herein is also to be understood as a disclosure of corresponding uses of materials involved in the method directed to the purpose of the method. Any of the oligomers comprising a GBS SIP- or CFB-target-hybridizing sequence and any combinations (e.g., kits and compositions) comprising such an oligomer are to be understood as also disclosed for use in detecting or quantifying GBS, and for use in the preparation of a composition for detecting or quantifying GBS.

Broadly speaking, methods may comprise one or more of the following components: target capture, in which GBS nucleic acid (e.g., from a sample, such as a clinical sample) is annealed to a capture oligomer; isolation, e.g., washing, to remove material not associated with a capture oligomer; amplification; and amplicon detection, e.g., amplicon quantification, which may be performed in real time with amplification. Certain embodiments involve each of the foregoing steps. Certain embodiments involve exponential amplification, optionally with a preceding linear amplification step. Certain embodiments involve exponential amplification and amplicon detection. Certain embodiments involve any two of the components listed above. Certain embodiments involve any two components listed adjacently above, e.g., washing and amplification, or amplification and detection.

In some embodiments, the present invention provides a method for determining the presence or absence of Group B *Streptococcus* (GBS) in a sample using an oligomer combination as described herein. Such a method generally includes (1) contacting the sample with at least two amplification oligomers for amplifying a GBS SIP or CFB nucleic acid target region corresponding to a SIP or CFB target nucleic acid, where the at least two amplification oligomers are as described above; (2) performing an in vitro nucleic acid amplification reaction, where any GBS SIP or CFB target nucleic acid present in the sample is used as a template for generating an amplification product; and (3) detecting the presence or absence of the amplification product, thereby determining the presence or absence of GBS in the sample. A detection method in accordance with the present invention typically further includes the step of obtaining the sample to be contacted with the at least two amplification oligomers. In certain embodiments, "obtaining" a sample to be used in steps (1)-(3) includes, for example, receiving the sample at a testing facility or other location where one or more steps of the method are performed, and/or retrieving the sample from a location (e.g., from storage or other depository) within a facility where one or more steps of the method are performed.

Amplifying a GBS target sequence utilizes an in vitro amplification reaction using at least two amplification oligomers that flank a target region to be amplified. In particular embodiments, the target region to be amplified is a GBS SIP target region substantially corresponding to SEQ ID NO:1 from about nucleotide position 56 to about nucleotide position 189 or from about nucleotide position 349 to about nucleotide position 489. Particularly suitable oligomer combinations for amplification of these GBS SIP target regions are described herein. For example, in some embodiments, an amplification oligomer combination for amplifying a SIP target region includes first and second SIP-specific amplification oligomers comprising, respectively, (A) a first SIP-specific target-hybridizing sequence that is SEQ ID NO:3 or a sequence substantially corresponding to SEQ ID NO:3, or an RNA equivalent or DNA/RNA chimeric thereof, and (B) a second SIP-specific target-hybridizing sequence that is SEQ ID NO:4 or a sequence substantially corresponding to SEQ ID NO:4, or an RNA equivalent or DNA/RNA chimeric thereof. In other embodiments, an amplification oligomer combination for amplifying a SIP target region includes first and second SIP-specific amplification oligomers comprising, respectively, (A) a first SIP-specific target-hybridizing sequence that is SEQ ID NO:7 or a sequence substantially corresponding to SEQ ID NO:7, or an RNA equivalent or DNA/RNA chimeric thereof, and (B) a second SIP-specific target-hybridizing sequence that is SEQ ID NO:8 or a sequence substantially corresponding to SEQ ID NO:8, or an RNA equivalent or DNA/RNA chimeric thereof.

In other embodiments, the target region to be amplified is a GBS CFB target region substantially corresponding to SEQ ID NO:2 from about nucleotide position 38 to about nucleotide position 151, from about nucleotide position 22 to about nucleotide position 151, from about nucleotide position 192 to about nucleotide position 329, or from about nucleotide position 585 to about nucleotide position 716. Particularly suitable oligomer combinations for amplification of these GBS CFB target regions are described herein. For example, in some embodiments, an amplification oligomer combination for amplifying a CFB target region includes first and second CFB-specific amplification oligomers comprising, respectively, (A) a first CFB-specific target-hybridizing sequence that is from about 17 to about 24 contiguous nucleotides and substantially corresponding to, or identical to, a sequence that is contained in the sequence of SEQ ID NO:26, or an RNA equivalent or DNA/RNA chimeric thereof, and (B) a second CFB-specific target-hybridizing sequence that is SEQ ID NO:13 or SEQ ID NO:15 or a sequence substantially corresponding to SEQ ID NO:13 or SEQ ID NO:15, or an RNA equivalent or DNA/RNA chimeric thereof; in more specific variations of such a first CFB-specific target-hybridizing sequence of (A), the CFB-specific target-hybridizing sequence is selected from (i) a sequence that substantially corresponds to, or is identical to, the sequence of SEQ ID NO:28 or SEQ ID NO:27, or an RNA equivalent or DNA/RNA chimeric thereof (e.g., a sequence that is SEQ ID NO:12 or SEQ ID NO:14 or a sequence that substantially corresponds to SEQ ID NO:12 or SEQ ID NO:14, or an RNA equivalent or DNA/RNA chimeric thereof), and (ii) a sequence that is SEQ ID NO:18 or a sequence substantially corresponding to SEQ ID NO:18, or an RNA equivalent or DNA/RNA chimeric thereof. In other embodiments, an amplification oligomer combination for amplifying a CFB target region includes first and second CFB-specific amplification oligomers comprising, respectively, (A) a first CFB-specific target-hybridizing sequence that is SEQ ID NO:16 or a sequence substantially corresponding to SEQ ID NO:16, or an RNA equivalent or DNA/RNA chimeric thereof, and (B) a second CFB-specific target-hybridizing sequence that is SEQ ID NO:17 or a sequence substantially corresponding to SEQ ID NO:17, or an RNA equivalent or DNA/RNA chimeric thereof. In other embodiments, an amplification oligomer combination for amplifying a CFB target region includes first and second CFB-specific amplification oligomers comprising, respectively, (A) a first CFB-specific target-hybridizing sequence that is SEQ ID NO:18 or a sequence substantially corresponding to SEQ ID NO:18, or an RNA equivalent or DNA/RNA chimeric thereof, and (B) a second CFB-specific target-hybridizing sequence that is SEQ ID NO:15 or a sequence substantially corresponding to SEQ ID NO:15, or an RNA equivalent or DNA/RNA chimeric thereof. In other embodiments, an amplification oligomer combination for amplifying a CFB target region includes first and second CFB-specific amplification oligomers comprising, respectively, (A) a first CFB-specific target-hybridizing sequence that is SEQ ID NO:20 or a sequence substantially corresponding to SEQ ID NO:20, or an RNA equivalent or DNA/RNA chimeric thereof, and (B) a second CFB-specific target-hybridizing sequence that is SEQ ID NO:21 or a sequence substantially corresponding to SEQ ID NO:21, or an RNA equivalent or DNA/RNA chimeric thereof.

A detection method in accordance with the present disclosure can further include the step of obtaining the sample to be subjected to subsequent steps of the method. In certain embodiments, "obtaining" a sample to be used includes, for example, receiving the sample at a testing facility or other location where one or more steps of the method are performed, and/or retrieving the sample from a location (e.g., from storage or other depository) within a facility where one or more steps of the method are performed.

In certain embodiments, the method further includes purifying the GBS target nucleic acid from other components in the sample, e.g., before an amplification, such as before a capture step. Such purification may include methods of separating and/or concentrating organisms contained in a sample from other sample components, or removing or degrading non-nucleic acid sample components, e.g., protein, carbohydrate, salt, lipid, etc. In some embodiments, DNA in the sample is degraded, e.g., with DNase, and optionally removing or inactivating the DNase or removing degraded DNA.

In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains GBS nucleic acid and other sample components Target capture typically occurs in a solution phase mixture that contains one or more capture probe oligomers that hybridize to the GBS SIP or CFB target sequence under hybridizing conditions. For embodiments comprising a capture probe tail, the GBS-target:capture-probe complex is captured by adjusting the hybridization conditions so that the capture probe tail hybridizes to an immobilized probe. Certain embodiments use a particulate solid support, such as paramagnetic beads.

Isolation can follow capture, where, for example, the complex on the solid support is separated from other sample components. Isolation can be accomplished by any appropriate technique, e.g., washing a support associated with the GBS SIP or CFB target-sequence one or more times (e.g., two or three times) to remove other sample components and/or unbound oligomer. In embodiments using a particulate solid support, such as paramagnetic beads, particles associated with the GBS target may be suspended in a washing solution and retrieved from the washing solution, in some embodiments by using magnetic attraction. To limit the number of handling steps, the GBS SIP or CFB target nucleic acid may be amplified by simply mixing the GBS target sequence in the complex on the support with amplification oligomers and proceeding with amplification steps.

Exponentially amplifying a GBS target sequence utilizes an in vitro amplification reaction using at least two amplification oligomers that flank a target region to be amplified. In some embodiments, at least first and second oligomers as described herein are provided. In some embodiments, a plurality of pairs of oligomers is provided; in some such variations, a plurality of oligomer pairs comprises oligomer pairs configured to hybridize to at least two GBS target nucleic acids (e.g., at least one oligomer pair configured to hybridized to a SIP target nucleic acid and at least one oligomer pair configured to hybridize to a CFB target nucleic acid). The amplification reaction can be cycled or isothermal. Suitable amplification methods include, for example, replicase-mediated amplification, polymerase chain reaction (PCR), ligase chain reaction (LCR), strand-displacement amplification (SDA), and transcription-mediated or transcription-associated amplification (TMA).

A detection step may be performed using any of a variety of known techniques to detect a signal specifically associated with the amplified target sequence, such as, e.g., by hybridizing the amplification product with a labeled detection probe and detecting a signal resulting from the labeled probe (including from label released from the probe following hybridization in some embodiments). In some embodiments, the labeled probe comprises a second moiety, such as a quencher or other moiety that interacts with the first label, as discussed above. The detection step may also provide additional information on the amplified sequence, such as, e.g., all or a portion of its nucleic acid base sequence. Detection may be performed after the amplification reaction is completed, or may be performed simultaneously with amplifying the target region, e.g., in real time. In one embodiment, the detection step allows homogeneous detection, e.g., detection of the hybridized probe without removal of unhybridized probe from the mixture (see. e.g., U.S. Pat. Nos. 5,639,604 and 5,283,174). In some embodiments, the nucleic acids are associated with a surface that results in a physical change, such as a detectable electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use nucleic acid detection probes that are configured to specifically hybridize to a sequence in the amplified product and detecting the presence of the probe:product complex, or by using a complex of probes that may amplify the detectable signal associated with the amplified products (e.g., U.S. Pat. Nos. 5,424,413; 5,451,503; and 5,849,481; each incorporated by reference herein). Directly or indirectly labeled probes that specifically associate with the amplified product provide a detectable signal that indicates the presence of the target nucleic acid in the sample. In particular, the amplified product will contain a target sequence in or complementary to a sequence in the GBS SIP or CFB gene, and a probe will bind directly or indirectly to a sequence contained in the amplified product to indicate the presence of GBS nucleic acid in the tested sample.

In embodiments that detect the amplified product near or at the end of the amplification step, a linear detection probe may be used to provide a signal to indicate hybridization of the probe to the amplified product. One example of such detection uses a luminescently labeled probe that hybridizes to target nucleic acid. Luminescent label is then hydrolyzed from non-hybridized probe. Detection is performed by chemiluminescence using a luminometer. (see, e.g., International Patent Application Pub. No. WO 89/002476, incorporated by reference herein). In other embodiments that use real-time detection, the detection probe may be a hairpin probe such as, for example, a molecular beacon, molecular torch, or hybridization switch probe that is labeled with a reporter moiety that is detected when the probe binds to amplified product (e.g., a dual-labeled hairpin probe comprising both a fluorescent label and a quenching moiety). In other embodiments for real-time detection, the detection probe is a linear oligomer such as, e.g., an oligomer labeled with both a fluorophore and a quenching moiety (e.g., a TaqMan probe). Such probes may comprise target-hybridizing sequences and non-target-hybridizing sequences. Various forms of such probes have been described previously (see, e.g., U.S. Pat. Nos. 5,210,015; 5,487,972; 5,118,801; 5,312,728; 5,925,517; 6,150,097; 6,849,412; 6,835,542; 6,534,274; and 6,361,945; and US Patent Application Pub. Nos. 20060068417A1 and 20060194240A1; each incorporated by reference herein).

Assays for detection of the GBS nucleic acid may optionally include a non-GBS internal control (IC) nucleic acid that is amplified and detected in the same assay reaction mixtures by using amplification and detection oligomers specific for the IC sequence. IC nucleic acid sequences can be, e.g., a DNA plasmid, an RNA template sequence (e.g., an in vitro transcript), or a synthetic nucleic acid that is spiked into a sample. Alternatively, the IC nucleic acid sequence may be a cellular component, which may be from exogenous cellular sources or endogenous cellular sources relative to the specimen. In these instances, an internal control nucleic acid is co-amplified with the GBS nucleic acid in the amplification reaction mixtures. The internal control amplification product and the GBS target sequence amplification product can be detected independently.

In certain embodiments, amplification and detection of a signal from an amplified IC sequence demonstrates that the assay reagents, conditions, and performance of assay steps were properly used in the assay if no signal is obtained for the intended target GBS nucleic acid (e.g., samples that test negative for GBS). An IC may also be used as an internal calibrator for the assay when a quantitative result is desired, i.e., the signal obtained from the IC amplification and detection is used to set a parameter used in an algorithm for quantitating the amount of GBS nucleic acid in a sample based on the signal obtained for an amplified GBS target sequence. ICs are also useful for monitoring the integrity of one or more steps in an assay. The primers and probe for the IC target sequence are configured and synthesized by using any well-known method provided that the primers and probe function for amplification of the IC target sequence and detection of the amplified IC sequence using substantially the same assay conditions used to amplify and detect the GBS target sequence. In preferred embodiments that include a target capture-based purification step, it is preferred that a target capture probe specific for the IC target be included in the assay in the target capture step so that the IC is treated in the assay in a manner analogous to that for the intended GBS analyte in all of the assay steps.

Also provided by the subject invention are formulations for determining the presence or absence of GBS in a sample. In some embodiments, a formulation is an aqueous formulation comprising (1) at least two SIP-specific or CFB-specific amplification oligomers for amplification of a SIP or CFB target region as described herein and (2) an organic buffer. An aqueous formulation for amplification of a GBS nucleic acid may include one or more additional components such as, e.g., a DNA polymerase enzyme, a reverse transcriptase enzyme, or a detection probe oligomer. In some embodiments, a formulation is an aqueous formulation comprising (1) a SIP-specific and/or CFB-specific detection probe oligomer as described herein and (2) on organic buffer. An aqueous formulation for comprising or more detection probe oligomers may include one or more additional components such as, e.g., a surfactant, a DNA polymerase enzyme, a reverse transcriptase enzyme, or at least one amplification oligomer. Particularly suitable surfactants include, for example, polyethylene glycol mono [4-(1,1,3, 3-tetramethylbutyl) phenyl] ether and polyoxyethylene sorbitan fatty acid esters (e.g., polysorbate 20, polysorbate 40, or polysorbate 60). In some embodiments, a surfactant in an aqueous detection probe formulation is a non-linear surfactant such as, for example, a polyoxyethylene sorbitan fatty acid ester (e.g., polysorbate 20, polysorbate 40, or polysorbate 60) or digitonin. An aqueous formulation as above for amplification or detection of GBS nucleic acid may further include a bulking agent such as, e.g., trehalose, raffinose, or a combination thereof. In some embodiments, an aqueous formulation as above contains at inorganic salt such as, e.g., magnesium, potassium, or sodium; in some such variations, the concentration of the inorganic salt is 4 mM or less. A particularly suitable organic buffer for an aqueous formulation as above is Tris (2-amino-2-(hydroxymethyl)-1,3-propanediol).

In a related aspect, for long-term storage, an aqueous formulation as described herein may be aliquoted into, e.g., vials, ampules, or other containers and dried (e.g., lyophilized) according to procedures known in the art. The dried product typically appears as a powder or cake. The containers are then sealed. Methods of preparing such dried formulations from the aqueous formulation, as well as the dried formulations prepared by such methods, are additional aspects of the present invention. In yet another aspect, the present invention provides a dried formulation that enables reconstitution into an aqueous formulation as described herein. Dried formulations for amplification or detection of GBS nucleic acid typically contain, in addition to one or more amplification oligomers and/or detection probes as described herein, a bulking agent such as, e.g., trehalose, raffinose, or a combination thereof. In some embodiments further comprising an inorganic salt, the percent mass of the inorganic salt to the mass of the dried formulation is 0.249% or less, 0.222% or less, or 0.195% or less. Methods of preparing a dried formulation from a lyophilized formulation as described herein are also encompassed by the present invention; such methods generally include dissolving the dried formulation in a suitable diluent (e.g., an organic buffer or water) to provide a reconstituted formulation.

Also provided by the subject invention is a reaction mixture for determining the presence or absence of a GBS target nucleic acid in a sample. A reaction mixture in accordance with the present disclosure includes one or both of (1) an oligomer combination as described herein for amplification of a GBS SIP and/or CFB target nucleic acid and (2) one or more detection probe oligomers as described herein for determining the presence or absence of a GBS SIP and/or CFB amplification product. The reaction mixture may further include a number of optional components such as, for example, capture probes, e.g., poly-(k) capture probes as described in US 2013/0209992, which is incorporated herein by reference. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, and dTTP; and/or ATP, CTP, GTP and UTP), and/or enzymes (e.g., a thermostable DNA polymerase, or reverse transcriptase and/or RNA polymerase), and will typically include test sample components, in which a GBS target nucleic acid may or may not be present. A reaction mixture may include amplification oligomers for only one target region of a GBS genome, or it may include amplification oligomers for multiple GBS target regions (e.g., both a SIP target region and a CFB target region). In addition, for a reaction mixture that includes a detection probe together with an amplification oligomer combination, selection of amplification oligomers and detection probe oligomers for a reaction mixture are linked by a common target region (i.e., the reaction mixture will include a probe that binds to a sequence amplifiable by an amplification oligomer combination of the reaction mixture). In some embodiments, a reaction mixture comprises an aqueous formulation as described above. In some embodiments, a reaction mixture is reconstituted with water or an organic buffer from a dried formulation as described above.

Also provided by the subject invention are kits for practicing the methods as described herein. A kit in accordance with the present disclosure includes one or both of (1) an oligomer combination as described herein for amplification of a GBS SIP and/or CFB target nucleic acid and (2) one or more detection probe oligomers as described herein for determining the presence or absence of a GBS SIP and/or CFB amplification product. In some embodiments, any oligomer combination described herein is present in the kit. The kits may further include a number of optional components such as, for example, capture probes, e.g., poly-(k) capture probes as described in US 2013/0209992. Other reagents that may be present in the kits include reagents suitable for performing in vitro amplification such as, e.g., buffers, salt solutions, appropriate nucleotide triphosphates (e.g., dATP, dCTP, dGTP, dTTP; and/or ATP, CTP, GTP and UTP), and/or enzymes (e.g., a thermostable DNA polymerase, or a reverse transcriptase and/or RNA polymerase). Oligomers as described herein may be packaged in a variety of different embodiments, and those skilled in the art will appreciate that the disclosure embraces many different kit configurations. For example, a kit may include amplification oligomers for only one target region of a GBS genome, or it may include amplification oligomers for multiple GBS target regions (e.g., both a SIP target region and a CFB target region). In addition, for a kit that includes a detection probe together with an amplification oligomer combination, selection of amplification oligomers and detection probe oligomers for a kit are linked by a common target region (i.e., the kit will include a probe that binds to a sequence amplifiable by an amplification oligomer combination of the kit). In certain embodiments, the kit further includes a set of instructions for practicing methods in accordance with the present disclosure, where the instructions may be associated with a package insert and/or the packaging of the kit or the components thereof.

The invention is further illustrated by the following non-limiting examples.

Example 1

Seventeen primer and probe combinations as shown in Table 2 were evaluated for *Streptococcus agalactiae* (GBS) detection in vitro.

TABLE 2

Primer and Probe Combinations

| Combination | Forward primer | Reverse Primer | Probe |
|---|---|---|---|
| 1 | SIP fwd 2 (SEQ ID NO: 3) | SIP rev2 (SEQ ID NO: 4) | SIP probe 2 (SEQ ID NO: 9) |
| 2 | SIP fwd 3 (SEQ ID NO: 5) | SIP rev3 (SEQ ID NO: 6) | SIP probe 3 (SEQ ID NO: 10) |
| 3 | SIP fwd 8 (SEQ ID NO: 7) | SIP rev8 bis (SEQ ID NO: 8) | SIP probe 8 (SEQ ID NO: 11) |
| 4 | CFB fwd1 (SEQ ID NO: 12) | CFB rev1 (SEQ ID NO: 13) | CFB probe 1 (SEQ ID NO: 22) |
| 5 | CFB fwd1 (SEQ ID NO: 12) | CFB rev1 (SEQ ID NO: 13) | CFB probe 1bis (SEQ ID NO: 23) |

TABLE 2-continued

Primer and Probe Combinations

| Combination | Forward primer | Reverse Primer | Probe |
|---|---|---|---|
| 6 | CFB fwd1 (SEQ ID NO: 12) | CFB rev2bis (SEQ ID NO: 15) | CFB probe 1 (SEQ ID NO: 22) |
| 7 | CFB fwd1 (SEQ ID NO: 12) | CFB rev2bis (SEQ ID NO: 15) | CFB probe 1bis (SEQ ID NO: 23) |
| 8 | CFB fwd2 (SEQ ID NO: 14) | CFB rev2bis (SEQ ID NO: 15) | CFB probe 1 (SEQ ID NO: 22) |
| 9 | CFB fwd2 (SEQ ID NO: 14) | CFB rev2bis (SEQ ID NO: 15) | CFB probe 1bis (SEQ ID NO: 23) |
| 10 | CFB fwd2 (SEQ ID NO: 14) | CFB rev1 (SEQ ID NO: 13) | CFB probe 1 (SEQ ID NO: 22) |
| 11 | CFB fwd2 (SEQ ID NO: 14) | CFB rev1 (SEQ ID NO: 13) | CFB probe 1bis (SEQ ID NO: 23) |
| 12 | CFB fwd3 (SEQ ID NO: 16) | CFB rev3 (SEQ ID NO: 17) | CFB probe 3 (SEQ ID NO: 24) |
| 13 | CFB fwd4 (SEQ ID NO: 18) | CFB rev1 (SEQ ID NO: 13) | CFB probe 1 (SEQ ID NO: 22) |
| 14 | CFB fwd4 (SEQ ID NO: 18) | CFB rev1 (SEQ ID NO: 13) | CFB probe 1bis (SEQ ID NO: 23) |
| 15 | CFB fwd4 (SEQ ID NO: 18) | CFB rev2bis (SEQ ID NO: 15) | CFB probe 1 (SEQ ID NO: 22) |
| 16 | CFB fwd4 (SEQ ID NO: 18) | CFB rev2bis (SEQ ID NO: 15) | CFB probe 1bis (SEQ ID NO: 23) |
| 17 | CFB fwd5 (SEQ ID NO: 20) | CFB rev5 (SEQ ID NO: 21) | CFB probe 5 (SEQ ID NO: 25) |

Materials and Methods.

As input material, an undefined GBS serotype from clinical culture was used. It was extracted in multiple replicates using the MagNA Pure 96 System (Roche). After extraction, the concentration of DNA was determined by OD 260/280 measurement. PCR was performed on the Applied Biosystems® (ABI) 7500 FAST Real-Time PCR System. The PCR profile used was as follows:

TABLE 3

PCR Profile

| 4 minutes | 95° C. | |
| 8 seconds | 95° C. | 45 cycles |
| 25 seconds | 60° C. | |

All samples were tested without the addition of an Internal Control to the samples. One concentration of the GBS target nucleic acid (1000 copies/µl in the PCR) was used and tested in four replicates. The concentration of primers was fixed at 600 nM and the probe concentration was 200 nM.

Results.

Cts and number of positive reactions for the different primer/probe combinations are shown in Table 4. The reported Ct is the cycle when the relative fluorescent unit (RFU) signal exceeds a set RFU threshold value.

TABLE 4

| Comb | Ct (average) | # of positive |
|---|---|---|
| 1 | 24.81 | 4/4 |
| 2 | / | 0/4 |
| 3 | 25.66 | 4/4 |
| 4 | 25.69 | 4/4 |
| 5 | 27.51 | 4/4 |
| 6 | 24.72 | 4/4 |
| 7 | 26.79 | 3/4 |
| 8 | 24.96 | 4/4 |
| 9 | 27.62 | 4/4 |
| 10 | 25.25 | 4/4 |
| 11 | 27.60 | 3/4 |
| 12 | 25.50 | 4/4 |
| 13 | 19.92 | 3/4 |
| 14 | 27.65 | 4/4 |
| 15 | 26.03 | 3/4 |
| 16 | 25.62 | 4/4 |
| 17 | 24.95 | 4/4 |

For each target gene, two combinations of primers and probes were selected for further evaluation, based on this data. For CFB, combinations 12 and 17 displayed the lowest Cts in combination with the highest RFU. For SIP, combinations 1 and 3 were selected. These combinations were tested on lower concentrations of GBS target nucleic acid allowing better discrimination. The results shown in Table 5 were obtained when testing 1, 10 and 100 copies/µl in the PCR.

TABLE 5

| Comb | Ct (average) 1 copy/µl | Ct (average) 10 copy/µl | Ct (average) 100 copy/µl |
|---|---|---|---|
| 1 | 39.19 | 35.22 | 31.77 |
| 3 | 37.41 | 33.61 | 30.36 |
| 12 | 38.34 | 35.02 | 32.41 |
| 17 | 38.44 | 35.10 | 31.70 |

Combinations, 1, 3, 12, and 17 were also tested on 1 and 10 copies/µl with different primer/probe concentrations (600/200 nM, 400/150 nM and 300/100 nM). Table 6 shows the results obtained using these different concentrations.

TABLE 6

| | 600/200 nM | | 400/150 nM | | 300/100 nM | |
|---|---|---|---|---|---|---|
| Comb | Ct (average) 1 copy/µl | Ct (average) 10 copy/µl | Ct (average) 1 copy/µl | Ct (average) 10 copy/µl | Ct (average) 1 copy/µl | Ct (average) 10 copy/µl |
| 1 | 38.51 | 34.91 | 40.09 | 36.26 | 39.65 | 36.98 |
| 3 | 36.85 | 33.73 | 38.89 | 34.44 | 38.84 | 35.54 |
| 12 | 38.31 | 35.00 | 38.89 | 35.34 | 39.02 | 35.68 |
| 17 | 37.10 | 34.44 | 38.29 | 35.13 | 39.53 | 35.76 |

Conclusion.

Based on the results summarized above, primer/probe combinations 3 and 17 (for the SIP and CFB target genes, respectively) were selected for further evaluation for sensitivity and specificity. These primer combinations were able to detect five (5) theoretical copies per PCR reaction at a Ct of 36-37.

Example 2

For the detection of internal control, two primer and probe combinations were evaluated: the SD-PLP/GIC combination and the New-GIC combination having the primer and probe sequences as shown in Table 7. The first step was to check which oligo set gave the best results when using Cy5 as a fluorophore and at which concentration. The second step focused on the selection of the concentration with the QUASAR®705 dye. On the automated PANTHER FUSION® system, the Cy5 dye gives low signals and should be detected using a QUASAR705 dye. Because the signal of the Cy5 is different from the signal generated by QUASAR705, the concentration of the primers and probes was re-evaluated.

TABLE 7

Internal Control Primers and Probes

| Name | Sequence (5'-3') |
|---|---|
| SD-PLP-Fwd | ACAGACAATGGCAGCAATTTCACCAG (SEQ ID NO: 29) |
| SD-PLP-Rev | CTCTTCTTTGTCTCTAATTGACC (SEQ ID NO: 30) |
| GIC Probe | AAACATCGCAAGTGCCACAAGCTT (SEQ ID NO: 31) |
| New-GIC-3F | TGGTAGCAGTTCATGTAGCCA (SEQ ID NO: 32) |
| New-GIC-3R | CTGGCCATCTTCCTGCTAAT (SEQ ID NO: 33) |
| New-GIC-3_P | TTCCTGCCCTGTTTCTGCTGGA (SEQ ID NO: 34) |

The initial testing of the primers and probes was performed on the ABI 7500 FAST Real-Time PCR System after KINGFISHER™ extraction. Three different primer/probe concentrations were used: 600/200 nM, 400/150 nM and 300/100 nM. In addition, the IC oligos were tested in combination with the SIP oligos when a GBS target is present (serotype II and IV: strains obtained from the CHU de Liege). The second step of the IC testing was performed on the BioRad CFX-96 qPCR device, which is capable of detecting both Cy5 and QUASAR705. Initially, the QUASAR705 combination was tested in comparison to the Cy5 combination to define the final concentration of the primers and probes.

Data from the initial testing showed that the New-GIC combination rendered higher signals than the SD-PLP/GIC combination. The New-GIC combination (300/100 nM) was further tested in the presence of SIP primers (600/200 nM) and different GBS types (serotype II and IV in $10^{\wedge}6$, $10^{\wedge}5$, $10^{\wedge}4$ dilutions). The data from this test showed that there is no significant impact on the presence of the IC primers and probes on GBS detection. In the same way, the IC signals were not influenced by the presence of a higher concentration of GBS. Based on the data, the SIP combination at 600/200 nM (FAM) was selected in combination with the IC New-GIC combination at 300/100 nM (Cy5).

A comparison between the Cy5 and QUSAR705 dye was made on the BioRad CFX-96. This data showed good compliance between both conditions. The New-GIC QUASAR705 at 400/150 nM combination was used for further testing on GBS strains.

In the following experiment, the SIP (600/200 nM) and New-GIC (400/150 nM) oligos were tested on serial dilutions of the different GBS serotypes (clinical cultures collected at University Hospital Center of Liège, University area of Sart Tilman, Building B 35, B-4000 Liege Belgium). Table 8 below reports ct values and shows overall low standard deviations between the different serotypes and the different dilutions for both the SIP target as well as for the New-GIC target.

TABLE 8

| Strain | Analysis | Dilution $10^{\wedge}6$ | | Dilution $10^{\wedge}5$ | | Dilution $10^{\wedge}4$ | |
|---|---|---|---|---|---|---|---|
| | | QUASAR705 | FAM | QUSASR705 | FAM | QUASAR705 | FAM |
| Ia | Mean | 31.20 | 37.01 | 28.21 | 32.58 | 30.12 | 28.86 |
| | STDev | 0.95 | 1.19 | 0.20 | 0.49 | 1.62 | 1.28 |
| Ib | Mean | 30.76 | 37.71 | 28.39 | 32.89 | 32.62 | 30.13 |
| | STDev | 0.90 | 0.85 | 0.27 | 0.36 | 1.02 | 0.29 |
| II | Mean | 30.13 | 37.16 | 28.37 | 32.59 | 31.09 | 30.03 |
| | STDev | 0.77 | 0.85 | 0.30 | 0.18 | 0.22 | 0.27 |
| III | Mean | 30.05 | 37.45 | 28.70 | 33.60 | 30.01 | 30.16 |
| | STDev | 0.92 | 0.59 | 0.25 | 0.36 | 0.59 | 1.09 |
| IV | Mean | 30.00 | 36.84 | 28.44 | 33.02 | 29.38 | 28.92 |
| | STDev | 0.62 | 0.40 | 0.09 | 0.18 | 0.53 | 1.57 |
| V | Mean | 30.26 | 37.34 | 28.86 | 33.26 | 29.53 | 29.12 |
| | STDev | 0.55 | 0.03 | 0.33 | 0.18 | 0.44 | 0.88 |
| VI | Mean | 29.84 | 37.83 | 28.51 | 34.63 | 30.62 | 32.15 |
| | STDev | 0.55 | 0.52 | 0.30 | 0.34 | 0.47 | 0.54 |
| VII | Mean | 30.36 | 38.05 | 28.41 | 33.38 | 30.40 | 30.48 |
| | STDev | 0.43 | 0.36 | 0.37 | 0.36 | 1.35 | 0.98 |
| VIII | Mean | 30.82 | 37.77 | 28.20 | 32.77 | 29.86 | 29.45 |
| | STDev | 1.02 | 0.34 | 0.72 | 0.55 | 1.00 | 1.54 |
| IX | Mean | 30.77 | 38.69 | 28.67 | 35.04 | 29.62 | 30.63 |
| | STDev | 0.44 | 0.09 | 0.42 | 0.30 | 1.08 | 1.26 |
| Overall | Mean | 30.42 | 37.58 | 28.48 | 33.38 | 30.32 | 29.99 |
| | STDev | 0.22 | 0.36 | 0.17 | 0.13 | 0.45 | 0.48 |

Example 3

This Example describes evaluation of the specificity and sensitivity of primer/probe combination 3, targeting the GBS SIP gene.

The SIP+New-GIC (Cy5) mix was used to test different samples on the ABI 7500 FAST Real-Time PCR System after extraction in the KINGFISHER™ system. The PCR profile shown in Table 3, supra, was used.

For specificity, the strains shown in Table 9 were evaluated for cross-reactivity.

TABLE 9

| Strain ID | Name | ATCC# | Sample Format | Stock Concentration |
|---|---|---|---|---|
| 1 | Acinetobacter lwoffii | 15309 | Lysate | 1E+08 CFU/mL |
| 2 | Actinomyces israelii | 12102 | Lysate | 1E+08 CFU/mL |
| 3 | Alcaligenes faecalis ssp. faecalis | 8750 | Lysate | 1E+08 CFU/mL |
| 4 | Atopobium vaginae | BAA-55 | Lysate | 5E+11 copies rRNA/mL |
| 5 | Bacteroides fragilis | 25285 | Lysate | 5E+08 CFU/mL |
| 6 | Bifidobacterium adolescentis | 15703 | Lysate | 1E+08 CFU/mL |
| 7 | Campylobacter jejuni ssp. jejuni | 33560 | Lysate | 1E+08 CFU/mL |
| 8 | Candida albicans | 18804 | Lysate | 1E+08 CFU/mL |
| 9 | Chlamydia trachomatis | VR-878 | Lysate | 9.3E+06 IFU/mL |
| 10 | Clostridium difficile | 9689 | Lysate | 1E+08 CFU/mL |
| 11 | Corynebacterium genitalium | 33030 | Lysate | 1E+08 CFU/mL |
| 12 | Cryptococcus neoformans | 32045 | Lysate | 1E+08 CFU/mL |
| 13 | Enterobacter cloacae | 13047 | Lysate | 1E+08 CFU/mL |
| 14 | Enterococcus faecalis | 19433 | Lysate | 1E+08 CFU/mL |
| 15 | Escherichia coli | 11775 | Lysate | 1E+08 CFU/mL |
| 16 | Fusobacterium nucleatum ssp. nucleatum | 25586 | Lysate | 1E+08 CFU/mL |
| 17 | Gardnerella vaginalis | 14018 | Lysate | 1E+08 CFU/mL |
| 18 | Haemophilus ducreyi | 33940 | Lysate | 1E+08 CFU/mL |
| 19 | Klebsiella pneumoniae | 23357 | Lysate | 1E+08 CFU/mL |
| 20 | Lactobacillus acidophilus | 4356 | Lysate | 1E+08 CFU/mL |
| 21 | Lactobacillus crispatus | 33820 | Lysate | 1E+08 CFU/mL |
| 22 | Listeria monocytogenes | 15313 | Lysate | 1E+08 CFU/mL |
| 23 | Mobiluncus curtisii | 35241 | Lysate | 5E+11 copies rRNA/mL |
| 24 | Mycoplasma hominis | 23114 | Lysate | 5E+11 copies rRNA/mL |
| 25 | Neisseria gonorrhoeae | 19424 | Lysate | 1E+08 CFU/mL |
| 26 | Pentatrichomonas hominis | 30000 | Lysate | 2.5E+07 Cells/mL |
| 27 | Peptostreptococcus magnus (Finegoldia magna) | 29328 | Lysate | 1E+08 CFU/mL |
| 28 | Prevotella bivia | 29303 | Lysate | 1E+08 CFU/mL |
| 29 | Propionibacterium acnes | 6919 | Lysate | 1E+08 CFU/mL |
| 30 | Proteus vulgaris | 8427 | Lysate | 1E+08 CFU/mL |
| 31 | Pseudomonas aeruginosa | 10145 | Lysate | 1E+08 CFU/mL |
| 32 | Staphylococcus aureus ssp. aureus | 12600 | Lysate | 1E+08 CFU/mL |
| 33 | Staphylococcus epidermidis | 14990 | Lysate | 1E+08 CFU/mL |
| 34 | Streptococcus agalactiae | 13813 | Lysate | 5E+08 CFU/mL |
| 35 | Streptococcus pyogenes | 12344 | Lysate | 1E+08 CFU/mL |
| 36 | Trichomonas tenax | 30207 | Lysate | 4.6E+07 Cells/mL |
| 37 | Ureaplasma urealyticum | 27618 | Lysate | 4.1E+11 Copies rRNA/mL |

For inclusivity, the GBS serotypes shown in Table 10 were tested.

TABLE 10

| Strain ID | Name | ATCC# | Stock Concentration |
|---|---|---|---|
| 38 | Streptococcus agalactiae Serotype Ia | 12400 | 1E+08 CFU/mL |
| 39 | Streptococcus agalactiae Serotype Ib | BAA-1174 | 1E+08 CFU/mL |
| 40 | Streptococcus agalactiae Serotype Ic | 27591 | 1E+08 CFU/mL |
| 41 | Streptococcus agalactiae Serotype III | 12403 | 1E+08 CFU/mL |
| 42 | Streptococcus agalactiae Serotype IV | 49446 | 5E+08 CFU/mL |
| 43 | Streptococcus agalactiae Type Strain | 13813 | 5E+08 CFU/mL |
| 44 | Streptococcus anginosus | 33397 | 1E+08 CFU/mL |
| 45 | Streptococcus bovis | 33317 | 1E+08 CFU/mL |
| 46 | Streptococcus gordonii | 33399 | 1E+08 CFU/mL |
| 47 | Streptococcus mitis | 49456 | 1E+08 CFU/mL |
| 48 | Streptococcus mutans | 25175 | 1E+08 CFU/mL |
| 49 | Streptococcus oralis | 10557 | 1E+08 CFU/mL |
| 50 | Streptococcus parasanguinis | 15911 | 1E+08 CFU/mL |
| 51 | Streptococcus pneumoniae | 33400 | 1E+08 CFU/mL |
| 52 | Streptococcus pyogenes | 12344 | 1E+08 CFU/mL |

TABLE 10-continued

| Strain ID | Name | ATCC# | Stock Concentration |
|---|---|---|---|
| 53 | *Streptococcus agalactiae* Serotype II | 12973 | 1E+08 CFU/mL |
| 54 | *Streptococcus agalactiae* Serotype V | BAA-611 | 1E+08 CFU/mL |
| 55 | *Streptococcus agalactiae* Serotype VI | BAA-2671 | 1E+08 CFU/mL |
| 56 | *Streptococcus agalactiae* Serotype VII | BAA-2670 | 1E+08 CFU/mL |
| 57 | *Streptococcus agalactiae* Serotype VIII | BAA-2669 | 1E+08 CFU/mL |
| 58 | *Streptococcus agalactiae* Serotype IX | BAA-2668 | 1E+08 CFU/mL |
| 59 | *Streptococcus acidominimus* | 51725 | 1E+08 CFU/mL |
| 60 | *Streptococcus canis* | 43496 | 1E+08 CFU/mL |
| 61 | *Streptococcus cricetus* | 19642 | 1E+08 CFU/mL |
| 62 | *Streptococcus cristatus* | 51100 | 1E+08 CFU/mL |
| 63 | *Streptococcus downei* | 33748 | 1E+08 CFU/mL |
| 64 | *Streptococcus dysagalactiae* | 43078 | 1E+08 CFU/mL |
| 65 | *Streptococcus equi* subsp *equi* | 33398 | 1E+08 CFU/mL |
| 66 | *Streptococcus ratti* | 19645 | 1E+08 CFU/mL |
| 67 | *Streptococcus constellatus* | DSM 20575 | 1E+08 CFU/mL |
| 68 | *Streptococcus pseudoporcinus* | DSM 18513 | 1E+08 CFU/mL |

All GBS serotypes to be detected were initially tested at the given stock concentration. Afterwards, strains were also tested at lower concentrations (as low as 100 CFU/mL).

Table 11 below shows specificity data obtained on ABI 7500 FAST system. All tested bacteria showed no interaction with the SIP primers and probes. The effectiveness of the PCR was evaluated by a positive control, which rendered positive signals.

TABLE 11

| Strain | Ct mean | Std Dev |
|---|---|---|
| *Acinetobacter lwoffii* | — | — |
| *Actinomyces israelii* | — | — |
| *Alcaligenes faecalis* ssp. *faecalis* | — | — |
| *Atopobium vaginae* | — | — |
| *Bacteroides fragilis* | — | — |
| *Bifidobacterium adolescentis* | — | — |
| *Campylobacter jejuni* ssp. *jejuni* | — | — |
| *Candida albicans* | — | — |
| *Chlamydia trachomatis* | — | — |
| *Clostridium difficile* | — | — |
| *Corynebacterium genitalium* | — | — |
| *Cryptococcus neoformans* | — | — |
| *Enterobacter cloacae* | — | — |
| *Enterococcus faecalis* | — | — |
| *Escherichia coli* | — | — |
| *Fusobacterium nucleatum* ssp. *nucleatum* | — | — |
| *Gardnerella vaginalis* | — | — |
| *Haemophilus ducreyi* | — | — |
| *Klebsiella pneumoniae* | — | — |
| *Lactobacillus acidophilus* | — | — |
| *Lactobacillus crispatus* | — | — |
| *Listeria monocytogenes* | — | — |
| *Mobiluncus curtisii* | — | — |
| *Mycoplasma hominis* | — | — |
| *Neisseria gonorrhoeae* | — | — |
| *Pentatrichomonas hominis* | — | — |
| *Peptostreptococcus magnus* (*Finegoldia magna*) | — | — |
| *Prevotella bivia* | — | — |
| *Propionibacterium acnes* | — | — |
| *Proteus vulgaris* | — | — |
| *Pseudomonas aeruginosa* | — | — |
| *Staphylococcus aureus* ssp. *aureus* | — | — |
| *Staphylococcus epidermidis* | — | — |
| *Streptococcus pyogenes* | — | — |
| *Trichomonas tenax* | — | — |
| *Ureaplasma urealyticum* | — | — |
| *Streptococcus anginosus* | — | — |
| *Streptococcus bovis* | — | — |
| *Streptococcus gordonii* | — | — |
| *Streptococcus mitis* | — | — |
| *Streptococcus mutans* | — | — |
| *Streptococcus oralis* | — | — |
| *Streptococcus parasanguinis* | — | — |
| *Streptococcus pneumoniae* | — | — |
| *Streptococucs pyogenes* | — | — |
| Negative Control | — | — |
| Positive Control | 31.875 | 0.318 |
| Positive Control | 30.840 | 0.184 |

An initial set tested at high concentrations on ABI 7500 FAST system gave the results shown in Table 12.

TABLE 12

| Strain | Ct mean | Std Dev |
|---|---|---|
| *Streptococcus agalactiae* Serotype Ia | 16.705 | 0.007 |
| *Streptococcus agalactiae* Serotype Ib | 17.655 | 0.120 |
| *Streptococcus agalactiae* Serotype Ic | 17.715 | 0.332 |
| *Streptococcus agalactiae* Serotype III | 18.240 | 0.141 |
| *Streptococcus agalactiae* Serotype IV | 15.740 | 0.014 |
| *Streptococcus agalactiae* Type Strain | 15.550 | 0.057 |

Table 13 below shows data obtained when GBS strains were tested at lower concentrations (100 CFU/ml in the sample).

TABLE 13

| Serotype | Concentration | Mean Ct +/− Std Dev |
|---|---|---|
| Serotype Ia | 100 CFU/ml in sample | 38.6 +/− 1.9 |
| Serotype Ib | 100 CFU/ml in sample | 38.1 +/− 1.4 |
| Serotype Ic | 100 CFU/ml in sample | 37.7 +/− 0.4 |
| Serotype III | 100 CFU/ml in sample | 37.9 +/− 0.6 |
| Serotype IV | 100 CFU/ml in sample | 38.1 +/− 1.6 |

These serotypes (Ia, Ib, Ic, III, IV) were further used to test the PCR efficiency. To this end, a serial dilution of these serotypes was prepared (ranging from $10^6$ CFU/ml to $10^1$ CFU/ml) and extracted on the MagNA Pure 96 System (Roche) and PCR performed on the ABI 7500 FAST system. The data showed the expected slope at approximately −3.3 and an efficiency between 92 and 98% between the different serotypes. Further the data confirmed the detection of all serotypes at 100 CFU/ml in the sample.

Example 4

This Example describes evaluation of the specificity of primer/probe combination 3, targeting the GBS SIP gene, on the automated PANTHER FUSION® system.

To evaluate specificity, the GBS strains shown in Table 15 below were tested directly on the PANTHER FUSION system, without the addition of extra STM or Lim Broth. The cartridges used contained SIP oligos and Cy5 oligos for the IC detection.

TABLE 15

| Strain ID | Strain Name | ATCC# | Sample Format | Concentration |
|---|---|---|---|---|
| 53 | *Streptococcus agalactiae* Serotype II | 12973 | Lysate | 1E+08 CFU/mL |
| 54 | *Streptococcus agalactiae* Serotype V | BAA-611 | Lysate | 1E+08 CFU/mL |
| 55 | *Streptococcus agalactiae* Serotype VI | BAA-2671 | Lysate | 1E+08 CFU/mL |
| 56 | *Streptococcus agalactiae* Serotype VII | BAA-2670 | Lysate | 1E+08 CFU/mL |
| 57 | *Streptococcus agalactiae* Serotype VIII | BAA-2669 | Lysate | 1E+08 CFU/mL |
| 58 | *Streptococcus agalactiae* Serotype IX | BAA-2668 | Lysate | 1E+08 CFU/mL |
| 59 | *Streptococcus acidominimus* | 51725 | Lysate | 1E+08 CFU/mL |
| 60 | *Streptococcus canis* | 43496 | Lysate | 1E+08 CFU/mL |
| 61 | *Streptococcus cricetus* | 19642 | Lysate | 1E+08 CFU/mL |
| 62 | *Streptococcus cristatus* | 51100 | Lysate | 1E+08 CFU/mL |
| 63 | *Streptococcus downei* | 33748 | Lysate | 1E+08 CFU/mL |
| 64 | *Streptococcus dysagalactiae* | 43078 | Lysate | 1E+08 CFU/mL |
| 65 | *Streptococcus equi* subsp *equi* | 33398 | Lysate | 1E+08 CFU/mL |
| 66 | *Streptococcus ratti* | 19645 | Lysate | 1E+08 CFU/mL |

All GBS serotypes (53 to 58) were detected in the FAM channel, while the other strains (59-66) were negative and provided only IC signals in the RED647 channel. This confirmed the specificity of the SIP oligos for the strains tested.

Additionally, using the same cartridges (SIP+IC (Cy5)) and testing on the PANTHER FUSION system, other potential cross-reactive bacteria and the remaining GBS serotypes, as shown in Table 16, were also tested.

TABLE 16

| Strain ID | Strain Name | ATCC# | Sample Format | Concentration |
|---|---|---|---|---|
| 1 | *Acinetobacter lwoffii* | 15309 | Lysate | 1E+08 CFU/mL |
| 2 | *Actinomyces israelii* | 12102 | Lysate | 1E+08 CFU/mL |
| 3 | *Alcaligenes faecalis* ssp. *faecalis* | 8750 | Lysate | 1E+08 CFU/mL |
| 4 | *Atopobium vaginae* | BAA-55 | Lysate | 5E+11 copies rRNA/mL |
| 5 | *Bacteroides fragilis* | 25285 | Lysate | 5E+08 CFU/mL |
| 6 | *Bifidobacterium adolescentis* | 15703 | Lysate | 1E+08 CFU/mL |
| 7 | *Campylobacter jejuni* ssp. *jejuni* | 33560 | Lysate | 1E+08 CFU/mL |
| 8 | *Candida albicans* | 18804 | Lysate | 1E+08 CFU/mL |
| 9 | *Chlamydia trachomatis* | VR-878 | Lysate | 9.3E+06 IFU/mL |
| 10 | *Clostridium difficile* | 9689 | Lysate | 1E+08 CFU/mL |
| 11 | *Corynebacterium genitalium* | 33030 | Lysate | 1E+08 CFU/mL |
| 12 | *Cryptococcus neoformans* | 32045 | Lysate | 1E+08 CFU/mL |
| 13 | *Enterobacter cloacae* | 13047 | Lysate | 1E+08 CFU/mL |
| 14 | *Enterococcus faecalis* | 19433 | Lysate | 1E+08 CFU/mL |
| 15 | *Escherichia coli* | 11775 | Lysate | 1E+08 CFU/mL |
| 16 | *Fusobacterium nucleatum* ssp. *nucleatum* | 25586 | Lysate | 1E+08 CFU/mL |
| 17 | *Gardnerella vaginalis* | 14018 | Lysate | 1E+08 CFU/mL |
| 18 | *Haemophilus ducreyi* | 33940 | Lysate | 1E+08 CFU/mL |
| 19 | *Klebsiella pneumoniae* | 23357 | Lysate | 1E+08 CFU/mL |
| 20 | *Lactobacillus acidophilus* | 4356 | Lysate | 1E+08 CFU/mL |
| 21 | *Lactobacillus crispatus* | 33820 | Lysate | 1E+08 CFU/mL |
| 22 | *Listeria monocytogenes* | 15313 | Lysate | 1E+08 CFU/mL |
| 23 | *Mobiluncus curtisii* | 35241 | Lysate | 5E+11 copies rRNA/mL |
| 24 | *Mycoplasma hominis* | 23114 | Lysate | 5E+11 copies rRNA/mL |
| 25 | *Neisseria gonorrhoeae* | 19424 | Lysate | 1E+08 CFU/mL |
| 26 | *Pentatrichomonas hominis* | 30000 | Lysate | 2.5E+07 Cells/mL |
| 27 | *Peptostreptococcus magnus* (*Finegoldia magna*) | 29328 | Lysate | 1E+08 CFU/mL |
| 28 | *Prevotella bivia* | 29303 | Lysate | 1E+08 CFU/mL |
| 29 | *Propionibacterium acnes* | 6919 | Lysate | 1E+08 CFU/mL |
| 30 | *Proteus vulgaris* | 8427 | Lysate | 1E+08 CFU/mL |
| 31 | *Pseudomonas aeruginosa* | 10145 | Lysate | 1E+08 CFU/mL |

TABLE 16-continued

| Strain ID | Strain Name | ATCC# | Sample Format | Concentration |
|---|---|---|---|---|
| 32 | Staphylococcus aureus ssp. aureus | 12600 | Lysate | 1E+08 CFU/mL |
| 33 | Staphylococcus epidermidis | 14990 | Lysate | 1E+08 CFU/mL |
| 34 | Streptococcus agalactiae | 13813 | Lysate | 5E+08 CFU/mL |
| 35 | Streptococcus pyogenes | 12344 | Lysate | 1E+08 CFU/mL |
| 36 | Trichomonas tenax | 30207 | Lysate | 4.6E+07 Cells/mL |
| 37 | Ureaplasma urealyticum | 27618 | Lysate | 4.1E+11 Copies rRNA/mL |
| 38 | Streptococcus agalactiae Serotype Ia | 12400 | Lysate | 1E+08 CFU/mL |
| 39 | Streptococcus agalactiae Serotype Ib | BAA-1174 | Lysate | 1E+08 CFU/mL |
| 40 | Streptococcus agalactiae Serotype Ic | 27591 | Lysate | 1E+08 CFU/mL |
| 41 | Streptococcus agalactiae Serotype III | 12403 | Lysate | 1E+08 CFU/mL |
| 42 | Streptococcus agalactiae Serotype IV | 49446 | Lysate | 5E+08 CFU/mL |
| 43 | Streptococcus agalactiae Type Strain | 13813 | Lysate | 5E+08 CFU/mL |
| 44 | Streptococcus anginosus | 33397 | Lysate | 1E+08 CFU/mL |
| 45 | Streptococcus bovis | 33317 | Lysate | 1E+08 CFU/mL |
| 46 | Streptococcus gordonii | 33399 | Lysate | 1E+08 CFU/mL |
| 47 | Streptococcus mitis | 49456 | Lysate | 1E+08 CFU/mL |
| 48 | Streptococcus mutans | 25175 | Lysate | 1E+08 CFU/mL |
| 49 | Streptococcus oralis | 10557 | Lysate | 1E+08 CFU/mL |
| 50 | Streptococcus parasanguinis | 15911 | Lysate | 1E+08 CFU/mL |
| 51 | Streptococcus pneumoniae | 33400 | Lysate | 1E+08 CFU/mL |
| 52 | Streptococcus pyogenes | 12344 | Lysate | 1E+08 CFU/mL |

Strains 38 to 43 returned positive signals in the FAM channel, while the other strains only returned IC signals in the RED channel.

Example 5

The performance of primer/probe combination 3, targeting the GBS SIP gene only, was compared to that of both primer/probe combinations 3 and 17 (as a multiplex reaction), targeting both the SIP and CFB genes, respectively. Different concentrations of GBS primer/probe were tested on a GBS strain spiked in Specimen Transport Medium (STM) at 3000 CFU/PCR, using ABI 7500 FAST Real-Time PCR System after extraction in the KINGFISHER™ system. The nucleic acid isolation, amplification, and detection reactions were performed generally as described above. No significant difference in Ct values was observed between the SIP only primer/probe set and the SIP/CFB primer/probe set whereas the end-point fluorescence level was found to be higher using the multiplexed SIP/CFB primer/probe set relative to the SIP only primer/probe set.

Example 6

A preliminary study was performed to determine the Limit of Detection (LoD) of multiplexed SIP/CFB primer/probe combinations 3 and 17 on GBS serotype III (from ATCC) using a Probit analysis (Minitab® 17 Software).

The GBS strain serotype III was serially diluted in Lim Broth at eight concentrations (based on plating): 20,000.0, 10,000.0, 5,000.0, 2,500.0, 1,250.0, 625.0, 312.5 and 156.3 CFU/mL, starting from a previous GBS culture (stock solution in Specimen Transport Medium (STM)).

These eight dilutions were added in corresponding sample tubes as follows: 250.0 µL sample into 750.0 µL transfer solution (the transfer solution being a mix of STM+Target Capture Oligo (TCO) (at 1667 pmol/750 µL STM). Because of the final 1:4 dilution occurring in the sample tube, the final concentrations were 5,000.0, 2,500.0, 1,250.0, 625.0, 312.5, 156.3, 78.1 and 39.1 CFU/mL.

Each dilution was tested in 20 extraction and one PCR replicate, over two runs on the PANTHER FUSION® system. A positive control (mix of GBS SIP and CFB plasmids at 141 and 781 c/µL in STM) and a negative control (Lim Broth) control were also tested in one or two extraction and one PCR replicates, respectively.

The Probit analysis was performed based on the concentrations tested, the number of positive calls and the number of trials obtained per concentration, using the Minitab® 17 Software.

Three distribution modes were compared (LogNormal, Weibull and LogLogistic) and the one giving the best P values, i.e., close to 0.000 for the regression table and the closest to 1.000 for the goodness-of-fit tests, was selected, as summarized in Table 17 below. Based on this table, the Weibull distribution mode was used for determination of the LoD.

TABLE 17

| Parameters | Prohit Analysis using the Minitab ® 17 Software | | |
|---|---|---|---|
| | | | |
| Probit Analysis Distribution Mode | LogNormal | Weibull | LogLogistic |
| Regression Table (P value) (should be ≈0.000) | 0.000 | 0.000 | 0.000 |
| Goodness-of-Fit Tests | | | |
| Pearson (P value) (should be ≈1.000) | 0.975 | 0.999 | 0.927 |
| Deviance (P value) (should be ≈1.000) | 0.966 | 0.999 | 0.893 |

The results obtained on the PANTHER FUSION system are summarized in Table 18 below. The last dilution was removed from the statistical analysis.

TABLE 18

| CFU/mL | Mean Ct value (FAM) | SD | % Positive Calls | Mean Ct value (Red677) | SD | % Valid Calls |
|---|---|---|---|---|---|---|
| 20,000.0 | 33.3 | 0.8 | 100 | 31.5 | 0.4 | 100 |
| 10,000.0 | 34.1 | 0.5 | 100 | 31.5 | 0.3 | 100 |
| 5,000.0 | 34.8 | 0.7 | 100 | 31.6 | 0.4 | 100 |
| 2,500.0 | 35.7 | 1.2 | 100 | 31.5 | 0.4 | 100 |
| 1,250.0 | 37.6 | 1.0 | 95 | 31.5 | 0.4 | 100 |
| 625.0 | 37.6 | 1.6 | 65 | 31.4 | 0.3 | 100 |
| 312.5 | 38.9 | 0.8 | 40 | 31.4 | 0.3 | 100 |

The $LoD_{95\%}$ for GBS serotype III was found at 1,294 CFU/mL in LB, i.e., 324 CFU/mL in the test sample.

Example 7

Analytical sensitivity and inclusivity using SIP primer/probe combination 3 multiplexed with CFB primer/probe combination 17 was evaluated by testing serial dilutions of cell lysates in Lim Broth negative clinical matrix for GBS serotypes Ia, Ib, Ic, II, III, IV, V, VI, VII, VIII, and IX. Additionally, one non-hemolytic (NH) strain was evaluated. The 95% detection limit of the PANTHER FUSION® GBS assay for each serotype was determined using probit regression analysis and the predicted detection limits were confirmed across the 12 GBS serotypes. Microorganism cross-reactivity and interference was evaluated with 45 bacterial or fungal species, with and without the presence of GBS serotype III at 3× the LoD. A method comparison study was performed testing Lim Broth enriched specimens (n=255) collected from antepartum women receiving standard of care GBS culture screening from two different hospitals. The sensitivity and specificity versus culture was determined for the PANTHER FUSION GBS assay. Specimens with discrepant results were tested with the BDMax GBS assay. All testing was performed on the PANTHER FUSION system.

Analytical Sensitivity & Inclusivity.

Panels were created by spiking lysate stocks of known CFU/mL concentrations into Lim Broth enrichment matrix. Each panel was tested in replicates of 30 with each of three assay reagent lots using three PANTHER FUSION systems. The 50% and 95% predicted LoDs were estimated for each strain and reagent lot through Probit analysis, (shown in Table 19 below). LoDs are reported in Table 19 as CFU/mL in the Lim Broth sample (back-calculated from CFU/mL in the PANTHER FUSION test sample, which were 1:4 dilutions of Lim Broth in Specimen Transport Medium (STM)). Confirmation testing of the predicted detection limits was performed and ≥95% positivity was observed for all serotypes.

TABLE 19

| | Reagent Lot 1 | | Reagent Lot 2 | | Reagent Lot 3 | |
|---|---|---|---|---|---|---|
| GBS | 50% LoD (95% CI) in CFU/mL | 95% LoD (95% CI) in CFU/mL | 50% LoD (95% CI) in CFU/mL | 95% LoD (95% CI) in CFU/mL | 50% LoD (95% CI) in CFU/mL | 95% LoD (95% CI) in CFU/mL |
| Ia | 36.50 (28.67-44.79) | 137.37 (103.68-209.68) | 26.36 (19.74-33.39) | 123.33 (89.18-202.93) | 35.63 (28.67-43.02) | 109.16 (84.84-149.26) |
| Ib | 27.67 (20.47-35.27) | 140.47 (100.59-234.73) | 28.51 (22.08-35.26) | 104.35 (78.89-158.81) | 25.24 (18.81-32.05) | 116.49 (84.69-189.07) |
| Ic | 48.16 (40.74-55.65) | 103.90 (85.36-143.01) | 36.45 (29.27-44.21) | 119.52 (91.78-177.29) | 29.60 (22.45-37.26) | 136.31 (99.20-220.52) |
| II | 49.95 (40.31-60.41) | 179.02 (135.06-276.19) | 37.71 (29.45-46.50) | 152.98 (113.83-239.70) | 41.91 (33.35-51.08) | 154.27 (116.64-214.66) |
| III | 42.71 (33.94-52.32) | 168.00 (125.20-261.50) | 34.51 (26.60-43.19) | 162.49 (117.01-268.11) | 33.28 (26.54-40.53) | 109.63 (84.15-162.56) |
| IV | 26.35 (18.89-32.96) | 83.97 (63.02-130.42) | 21.61 (16.66-26.88) | 72.93 (54.81-113.53) | 23.38 (18.44-28.67) | 70.13 (53.84-105.00) |
| V | 32.80 (25.70-40.38) | 122.33 (92.24-186.80) | 31.85 (25.75-38.13) | 84.13 (66.53-121.30) | 28.89 (17.34-28.71) | 88.18 (65.55-138.81) |
| VI | 63.46 (50.73-78.03) | 281.95 (201.92-475.82) | 56.34 (44.56-69.76) | 265.87 (189.40-449.57) | 49.18 (38.97-60.64) | 216.19 (157.14-351.40) |
| VII | 57.96 (46.30-71.06) | 250.80 (180.16-424.80) | 41.29 (32.01-51.16) | 182.99 (133.94-295.79) | 29.36 (21.38-37.65) | 160.87 (113.94-275.73) |
| VIII | 44.28 (34.14-55.34) | 220.54 (157.50-370.98) | 51.86 (41.06-63.93) | 231.27 (167.30-380.88) | 38.63 (29.62-48.47) | 192.88 (137.94-322.17) |
| IX | 46.72 (35.16-59.69) | 300.99 (202.02-567.73) | 35.36 (26.76-44.70) | 186.19 (131.87-316.56) | 29.29 (21.95-37.01) | 137.93 (100.34-223.89) |
| NH | 63.97 (50.75-78.99) | 300.17 (211.99-522.99) | 57.05 (45.71-69.43) | 227.01 (167.33-366.40) | 54.15 (43.74-65.30) | 192.88 (145.53-299.61) |

Microorganism Cross-reactivity and Interference.

The bacterial and fungal species shown in Table 20 below were introduced into negative Lim Broth matrix at a concentration of 1e6 CFU/mL in the test sample. Panels were tested with and without GBS serotype III at 3× the estimated LoD. Each panel was tested in triplicate with one assay reagent lot. No cross-reactivity was observed in the panels void of GBS target. No interference was observed in the panels containing GBS target.

TABLE 20

| Organisms Tested |
| --- |
| *Acinetobacter iwoffii* |
| *Actinomycesisraelii* |
| *Alcaligenesfaecalis* |
| *Bifidobacterium adolescentis* |
| *Campylobacter jejuni* |
| *Candida albicans* |
| *Clostridium difficile* |
| *Corynebacterium genitalium* |
| *Cryptococcus neoformans* |
| *Enterobacter cloacae* |
| *Enterococcusfaecalis* |
| *Escherichia coli* |
| *Fusobacterium necleatum* |
| *Gardnerellavaginalis* |
| *Haemophilusducreyi* |
| *Klebsiellapneumoniae* |
| *Lactobacillus acidophilus* |
| *Lactobacilluscrispatus* |
| *Listeria monocytogenes* |
| *Neisseria gonorrhoeae* |
| *Peptostreptococcusmagnus* |
| *Prevolellabivia* |
| *Propionibacterium acnes* |
| *Proteus vulgaris* |
| *Pseudomonas aeruginosa* |
| *Staphylococcus aureus* |
| *Staphylococcus epidermidis* |
| *Streptococcus pyogenes* |
| *Streptococcus anginosus* |
| *Streptococcus bovis* |
| *Streptococcus gordonii* |
| *Streptococcus mitis* |
| *Streptococcus mutans* |
| *Streptococcus oralis* |
| *Streptococcus parasanguinis* |
| *Streptococcus pneumoniae* |
| *Streptococcus acidominimus* |
| *Streptococcus canis* |
| *Streptococcus cricetus* |
| *Streptococcus cristatus* |
| *Streptococcus downei* |
| *Streptococcus dysagalactiae* |
| *Streptococcus equi* |
| *Streptococcus ratti* |
| *Streptococcus costellatus* |

Method Comparison.

A total of 255 vaginal-rectal swabs were collected from antepartum women according to CDC recommended guidelines. Each specimen was enriched at 35-37° C. for 18 to 24 hours in Lim Broth media. Each specimen was evaluated using reference culture and tested in the PANTHER FUSION GBS assay. Clinical sensitivity and specificity was determined according to the reference culture result. Results are summarized in Table 21 below. Sensitivity and specificity of the PANTHER FUSION GBS assay were 100% and 98.6%, respectively. There were three culture negative, PANTHER FUSION GBS assay positive specimens, all for which repeat PANTHER FUSION GBS assay testing yielded positive results. A second molecular test method, the BDMax GBS assay, was used to analyse the discordant samples, and GBS was detected in all three samples.

TABLE 21

| | | Reference Culture | |
| --- | --- | --- | --- |
| | | + | − |
| PANTHER FUSION GBS Assay | + | 43 | 3 |
| | − | 0 | 209 |

Sensitivity (95% CI): 100% (91.8-100)
Specificity (95% CI): 98.6% (95.9-99.5)
Culture Prevalence: 16.9%
Panther Fusion Prevalence: 18.0%

Conclusions.

The preliminary analytical studies demonstrated that the assay had consistent detection of GBS across evaluated serotypes, and comparison with culture methods showed the assay to have high sensitivity and specificity.

Example 8

This Example describes evaluation of the analytical specificity of SIP primer/probe combination 3 multiplexed with CFB primer/probe combination 17 on the automated PANTHER FUSION® system.

A panel of 124 organisms consisting of 104 bacterial, 12 viral, 4 yeast/fungi and 4 protozoa/parasite strains representing microorganisms commonly found in vaginal/anal flora or that are the same family/genus as GBS were selected for analytical specificity testing. The analytical specificity panel is detailed in Table 22. Among the 124 selected organisms, 14 were not available for testing at the time of the study. The potential cross reactivity with the GBS assay primers and probes for those 14 unavailable organisms were assessed by BLAST analysis with no alignments identified.

Analytical specificity was assessed using the following two approaches:
  (1) Cross-reactivity (exclusivity): testing whether these organisms cross-react with the GBS assay primers and probes and induce a false positive result in the confirmed GBS negative samples;
  (2) Microbial Interference: testing whether these organisms could interfere with normal GBS detection in GBS positive samples at the concentration near LoD.

Pools consisting of five (5) microorganisms were diluted in Specimen Transport Medium (STM) at high concentrations (minimum $10^6$ CFU/mL for bacteria and yeast and $10^5$ PFU/mL for virus, or equivalent). Pool composition is detailed in Table 22. For the cross-reactivity (exclusivity) assessment, these pools of microorganisms were added to clinical negative Lim Broth matrix samples (GBS negative samples). For the microbial interference assessment, these pools of microorganisms were added to clinical negative Lim Broth matrix samples spiked with GBS serotype III at 3×LoD (GBS positive samples).

For each pool of microorganisms to be evaluated, three replicates of GBS-positive and GBS-negative samples were tested for PANTHER FUSION GBS assay and data reported.

Acceptance criteria:
  (1) For a (pool of) microorganism(s) to be considered as non-cross-reactive, the three replicates of clinical negative Lim Broth matrix samples (GBS negative samples) must be reported as negative;
  (2) For a (pool of) microorganism(s) to be considered as a non-interfering, the three replicates of GBS serotype III positive sample (GBS positive samples) must be reported as positive.

TABLE 22

| Analytical Specificity Panel | | |
|---|---|---|
| Microorganism | Conc. (CFU/mL or PFU/mL*) | Pool |
| *Bacillus cereus* | $1 \times 10^6$ | I |
| *Yersinia enterocolitica* subsp. *enterocolitica* | $1 \times 10^6$ | |
| *Anaerococcus prevotii* | $1 \times 10^6$ | |
| *Propionibacterium acnes* | $1 \times 10^6$ | |
| *Clostridium difficile* | $1 \times 10^6$ | |
| *Fusobacterium nucleatum* | $1 \times 10^6$ | II |
| *Bifidobacterium adolescentis* Reuter | $1 \times 10^6$ | |
| *Candida albicans* (NIH 3147) | $1 \times 10^6$ | |
| *Candida glabrata* (CBS 138) | $1 \times 10^6$ | |
| *Candida tropicalis* | $1 \times 10^6$ | |
| *Cryptococcus neoformans* | $1 \times 10^{5}$* | III |
| *Klebsiella pneumoniae* | $1 \times 10^6$ | |
| *Proteus mirabilis* | $1 \times 10^6$ | |
| *Alcaligenes faecalis* | $1 \times 10^6$ | |
| *Enterobacter aerogenes* | $1 \times 10^6$ | |
| *Stenotrophomonas maltophilia* | $1 \times 10^6$ | IV |
| *Campylobacter jejuni* | $1 \times 10^6$ | |
| *Providencia stuartii* | $1 \times 10^6$ | |
| *Micrococcus luteus* | $1 \times 10^6$ | |
| *Staphylococcus haemolyticus* | $1 \times 10^6$ | |
| *Enterococcus faecalis* | $1 \times 10^6$ | V |
| *Pseudomonas fluorescens* | $1 \times 10^6$ | |
| *Staphylococcus saprophyticus* | $1 \times 10^6$ | |
| *Proteus vulgaris* | $1 \times 10^6$ | |
| *Toxoplasma gondii* | $1 \times 10^{5}$* | |
| *Enterococcus faecium* | $1 \times 10^6$ | VI |
| *Escherichia coli* | $1 \times 10^6$ | |
| *Enterobacter cloacae* | $1 \times 10^6$ | |
| *Morganella morganii* | $1 \times 10^6$ | |
| *Shigella flexneri* | $1 \times 10^6$ | |
| *Streptococcus pyogenes* (group A) | $1 \times 10^6$ | VII |
| *Streptococcus ratti* | $1 \times 10^6$ | |
| *Staphylococcus lugdunensis* | $1 \times 10^6$ | |
| *Acinetobacter baumannii* | $1 \times 10^6$ | |
| *Staphylococcus aureus* | $1 \times 10^6$ | |
| *Staphylococcus epidermidis* | $1 \times 10^6$ | VIII |
| *Shigella sonnei* | $1 \times 10^6$ | |
| *Citrobacter freundii* | $1 \times 10^6$ | |
| *Enterococcus gallinarum* | $1 \times 10^6$ | |
| *Acinetobacter lwoffii* | $1 \times 10^6$ | |
| *Pseudomonas aeruginosa* | $1 \times 10^6$ | IX |
| *Streptococcus criceti* | $1 \times 10^6$ | |
| *Haemophilus influenzae* | $1 \times 10^6$ | |
| *Klebsiella oxytoca* | $1 \times 10^6$ | |
| *Streptococcus bovis* (group D) | $1 \times 10^6$ | |
| *Streptococcus parasanguinis* | $1 \times 10^6$ | X |
| *Streptococcus equi* subsp. *equi* (group D) | $1 \times 10^6$ | |
| *Enterococcus durans* | $1 \times 10^6$ | |
| *Lactobacillus plantarum* | $1 \times 10^6$ | |
| *Streptococcus dysgalactiae* | $1 \times 10^6$ | |
| *Streptococcus constellatus* | $1 \times 10^6$ | XI |
| *Streptococcus oralis* (oral group) | $1 \times 10^6$ | |
| *Bacillus coagulans* | $1 \times 10^6$ | |
| *Streptococcus pseudoporcinus* | $1 \times 10^6$ | |
| *Streptococcus mitis* (oral group) | $1 \times 10^6$ | |
| *Streptococcus anginosus* | $1 \times 10^6$ | XII |
| *Prevotella oralis* | $1 \times 10^6$ | |
| *Streptococcus canis* | $1 \times 10^6$ | |
| *Lactobacillus delbrueckii* subsp. *lactis* | $1 \times 10^6$ | |
| *Corynebacterium sp* (genitalium) | $1 \times 10^6$ | |
| *Neisseria gonorrhoeae* | $1 \times 10^6$ | XIII |
| *Streptococcus pneumoniae* (oral group) | $1 \times 10^6$ | |
| *Streptococcus mutans* (oral group) | $1 \times 10^6$ | |

TABLE 22-continued

| Analytical Specificity Panel | | |
|---|---|---|
| *Corynebacterium urealyticum* | $1 \times 10^6$ | |
| *Lactobacillus reuteri* | $1 \times 10^6$ | |
| *Lactobacillus* sp. | $1 \times 10^6$ | XIV |
| *Lactobacillus casei* | $1 \times 10^6$ | |
| *Lactobacillus acidophilus* | $1 \times 10^6$ | |
| *Streptococcus gordonii* (oral group) | $1 \times 10^6$ | |
| *Bulkholderia cepacia* | $1 \times 10^6$ | |
| *Aeromonas hydrophila* | $1 \times 10^6$ | XV |
| *Moraxella atlantae* | $1 \times 10^6$ | |
| *Prevotella bivia* | $1 \times 10^6$ | |
| *Pasteurella aerogenes* | $1 \times 10^6$ | |
| *Rhodococcus equi* | $1 \times 10^6$ | |
| *Listeria monocytogenes* | $1 \times 10^6$ | XVI |
| *Lactobacillus gasseri* | $1 \times 10^6$ | |
| *Peptoniphilus asaccharolyticus* | $1 \times 10^6$ | |
| *Atopobium vaginae* | $1 \times 10^6$ | |
| *Bifidobacterium brevis* | $1 \times 10^6$ | |
| *Abiotropha defectiva* | $1 \times 10^6$ | XVII |
| *Anaerococcus tetradius* | $1 \times 10^6$ | |
| *Finegoldia magna* | $1 \times 10^6$ | |
| *Peptostreptococcus anaerobius* | $1 \times 10^6$ | |
| *Anaerococcus lactolyticus* | $1 \times 10^6$ | |
| Human herpesvirus 4 (EB V) | $1 \times 10^{5*}$ | XVIII |
| *Bacteroides fragilis* | $1 \times 10^6$ | |
| *Bordetella pertussis* | $1 \times 10^6$ | |
| *Chlamydia trachomatis* | $1 \times 10^6$ | |
| Human herpesvirus 5 (CMV) | $1 \times 10^{5*}$ | |
| *Hafnia alvei* | $1 \times 10^6$ | XIX |
| *Trichomonas vaginalis* | $1 \times 10^{5*}$ | |
| Human immuno-deficiency virus-1 (HIV-1) | $1 \times 10^{5*}$ | |
| *Moraxella catarrhalis* | $1 \times 10^6$ | |
| *Mycoplasma genitalium* | $1 \times 10^6$ | |
| *Prevotella melaninogenica* | $1 \times 10^6$ | XX |
| Rubella Virus | $1 \times 10^{5*}$ | |
| *Serratia marcescens* | $1 \times 10^6$ | |
| *Streptococcus intermedius* | $1 \times 10^6$ | |
| Human papilloma Virus Type 16 (HPV16) | $1 \times 10^{5*}$ | |
| Hepatitis B Virus | $1 \times 10^{5*}$ | XXI |
| Hepatitis C Virus | $1 \times 10^{5*}$ | |
| Herpes Simplex Virus-1 (HSV-1) | $1 \times 10^{5*}$ | |
| Herpes Simplex Virus-2 (HSV-2) | $1 \times 10^{5*}$ | |
| Human herpesvirus 3 (VZV) | $1 \times 10^{5*}$ | |
| *Arcanobacterium pyogenes* | $1 \times 10^6$ | XXII |
| *Mobiluncus curtisii* subsp *curtisii* | $1 \times 10^6$ | |
| *Gardnerella vaginalis* | $1 \times 10^6$ | |
| *Salmonella enterica* subsp, *enterica* ser. dublin (group D) | $1 \times 10^6$ | |
| *Streptococcus acidominus* | $1 \times 10^6$ | |

| Microorganisms Assessed by BLAST Analysis | | |
|---|---|---|
| *Actinomyces israelii* | *Pantoea agglomerans* | Human immuno-deficiency virus-2 (HIV-2) |
| *Actinobacillus pleuropneumoniae* | *Staphylococcus simulans* | Parvovirus B19 |
| *Haemophilus ducreyi* | *Streptococcus cristatus* | *Pentatrichomonas hominis* |
| *Lactobacillus crispatus* | *Streptococcus downei* | *Trichomonas tenax* |
| *Mycoplasma hominis* | *Ureaplasma urealyticum* | |

*genomic extracts, concentration expressed in c/mL

Study Results.

The run was valid and the Internal Control (IC) was detected in each reaction, resulting in a 0% invalid run rate and a 0% IC invalid rate, respectively. All GBS negative samples tested for the cross-reactivity assessment gave negative, valid results with the GBS primers and probes on the PANTHER FUSION system, while all GBS positive samples tested for the microbial interference assessment gave GBS-positive results with the PANTHER FUSION GBS assay. Results are reported in Table 23 below.

TABLE 23

Analytical Specificity Results

% Positive/Valid call (replicate detected/valid reaction)

| Pool number | NoGBS | | GBS at 3x LoD | |
| --- | --- | --- | --- | --- |
| | GBS | IC | GBS | IC |
| No microorganism spiked | 0% (0/3) | 100% (3/3) | 100% (3/3) | 100% (3/3) |
| I | 0% (0/3) | 100% (3/3) | 100% (3/3) | 100% (3/3) |
| II | 0% (0/3) | 100% (3/3) | 100% (3/3) | 100% (3/3) |
| III | 0% (0/3) | 100% (3/3) | 100% (3/3) | 100% (3/3) |
| IV | 0% (0/3) | 100% (3/3) | 100% (3/3) | 100% (3/3) |
| V | 0% (0/3) | 100% (3/3) | 100% (3/3) | 100% (3/3) |
| VI | 0% (0/3) | 100% (3/3) | 100% (3/3) | 100% (3/3) |
| VII | 0% (0/3) | 100% (3/3) | 100% (3/3) | 100% (3/3) |
| VIII | 0% (0/3) | 100% (3/3) | 100% (3/3) | 100% (3/3) |
| IX | 0% (0/3) | 100% (3/3) | 100% (3/3) | 100% (3/3) |
| X | 0% (0/3) | 100% (3/3) | 100% (3/3) | 100% (3/3) |
| XI | 0% (0/3) | 100% (3/3) | 100% (3/3) | 100% (3/3) |
| XII | 0% (0/3) | 100% (3/3) | 100% (3/3) | 100% (3/3) |
| XIII | 0% (0/3) | 100% (3/3) | 100% (3/3) | 100% (3/3) |
| XIV | 0% (0/3) | 100% (3/3) | 100% (3/3) | 100% (3/3) |
| XV | 0% (0/3) | 100% (3/3) | 100% (3/3) | 100% (3/3) |
| XVI | 0% (0/3) | 100% (3/3) | 100% (3/3) | 100% (3/3) |
| XVII | 0% (0/3) | 100% (3/3) | 100% (3/3) | 100% (3/3) |
| XVIII | 0% (0/3) | 100% (3/3) | 100% (3/3) | 100% (3/3) |
| XIX | 0% (0/3) | 100% (3/3) | 100% (3/3) | 100% (3/3) |
| XX | 0% (0/3) | 100% (3/3) | 100% (3/3) | 100% (3/3) |
| XXI | 0% (0/3) | 100% (3/3) | 100% (3/3) | 100% (3/3) |
| XXII | 0% (0/3) | 100% (3/3) | 100% (3/3) | 100% (3/3) |

SEQUENCES

TABLE 24

Exemplary Oligomer Sequences, Reference Sequences, and Regions

| SEQ ID NO: | Description | Sequence (5' → 3') |
| --- | --- | --- |
| 1 | Reference Sequence corresponding to *Streptococcus agalactiae* (GBS) SIP gene | ATGAAAATGAATAAAAAGGTACTATTGACATCGACAATGGCAGCTT CGCTATTATCAGTCGCAAGTGTTCAAGCACAAGAAACAGATACGAC GTGGACAGCACGTACTGTTTCAGAGGTAAAGGCTGATTTGGTAAAG CAAGACAATAAATCATCATATACTGTGAAATATGGTGATACACTAA GCGTTATTTCAGAAGCAATGTCAATTGATATGAATGTCTTAGCAAA AATTAATAACATTGCAGATATCAATCTTATTTATCCTGAGACAACA CTGACAGTAACTTACGATCAGAAGAGTCACACTGCCACTTCAATGA AAATAGAAACACCAGCAACAAATGCTGCTGGTCAAACAACAGCTAC TGTGGATTTGAAAACCAATCAAGTTTCTGTTGCAGACCAAAAAGTT TCTCTCAATACAATTTCGGAAGGTATGACACCAGAAGCAGCACCAA CGATTGTTTCGCCAATGAAGACATATTCTTCTGCGCCAGCTTTGAA ATCAAAAGAAGTATTAGCACAAGAGCAAGCTGTTAGTCAAGCCGCA GCTAATGAACAGGTATCACCAGCTCCTGTGAAGTCGATTACTTCAG AAGTTCCAGCAGCTAAAGAGGAAGTTAAACCAACTCAGACGTCAGT CAGTCAGTCAACAACAGTATCACCAGCTTCTGTTGCCACTGAAACA CCAGCTCTAGTAGCTAAAGTAGCACCGGTAAGAACTGTAGCAGCCC CTAGAGTGACAAGTGCTAAAGTAGTCACTCCTAAAGTAGAAACTGG TGCATCACCAGAGCATGTATCAGCTCCAGCAGTTCCTGTGACTACG ACTTCAACAGCTACAGACAATAAGTTACAAGCGACTGAAGTTAAGA GCGTTCCGGTAGCACAAAAAGCTCCAACAGCAACACCGGTAGCACA ACCAGCTTCAACAACAAATGCAGTAGCTGCACATCCTGAAAATGCA GGGCTCCAACCTCATGTTGCAGCTTATAAAGAAAAAGTAGCGTCAA CTTATGGAGTTAATGAATTCAGTACATACCGTGCGGGAGATCCAGG TGATCATGGTAAAGGTTTAGCAGTTGACTTTATTGTAGGTACCAAT CAAGCACTTGGTAATGAAGTTGCACAGTACTCTACACAAAATATGG CAGCAAATAACATTTCATATGTTATCTGGCAACAAAAGTTTTACTC AAATACAAATAGTATTTATGGACCTGCTAATACTTGGAATGCAATG CCAGATCGTGGTGGCGTTACTGCCAACCACTATGACCACGTTCACG TATCATTTAACAAATAA |

TABLE 24-continued

Exemplary Oligomer Sequences, Reference Sequences, and Regions

| SEQ ID NO: | Description | Sequence (5' → 3') |
|---|---|---|
| 2 | Reference Sequence corresponding to *Streptococcus agalactiae* (GBS) CFB (cAMP-factor) gene | ATGAACGTTAAACATATGATGTATCTATCTGGAACTCGAGTGGCTG GTGCATTGTTATTTTCACCAGCTGTATTAGAAGTACATGCTGATCA AGTGACAACTCCACAAGTGGTAAATCAAGTAAATAGTAATAATCAA GCCCAGCAAATGGCTCAAAAGCTTGATCAAGATAGCATTCAGTTGA GAAATATCAAAGATAATGTTCAGGGAACAGATTATGAAAAACCGGT TAATGAGGCTATTACTAGCGTTGAAAAATTAAAGACTTCATTGCGT GCCAACCCTGAGACAGTTTATGATTTGAATTCTATTGGTAGTCGTG TAGAAGCCTTAACAGATGTGATTGAAGCAATCACTTTTTTCAACTCA ACATTTAACAAATAAGGTTAGTCAAGCAAATATTGATATGGGATTT GGGATAACTAAGCTAGTTATTCGCATTTTAGATCCATTTGCTTCAG TTGATTCAATTAAAGCTCAAGTTAACGATGTAAAGGCATTAGAACA AAAGGTTTTAACTTATCCTGATTTAAAACCAACTGATAGAGCTACC ATCTACACAAAATCAAAACTTGATAAGGAAATTTGGAATACACGTT TTACTAGAGATAAAAAAGTACTTAACGTCAAAGAATTTAAAGTTTA CAATACTTTAAATAAAGCAATCACACATGCTGTTGGAGTTCAGTTG AATCCAAATGTTACGGTACAACAAGTTGATCAAGAGATTGTAACAT TACAAGCAGCACTTCAAACAGCATTAAAATAA |
| 3 | SIP forward primer | CAGTCGCAAGTGTTCAAGC |
| 4 | SIP reverse primer | AACGCTTAGTGTATCACCATAT |
| 5 | SIP forward primer | CGGTAAGAACTGTAGCAGCC |
| 6 | SIP reverse primer | GCTCTTAACTTCAGTCGCTTG |
| 7 | SIP forward primer | AACAAATGCTGCTGGTCAAA |
| 8 | SIP reverse primer | AGAATATGTCTTCATTGGCGAA |
| 9 | SIP detection probe | ACTGTTTCAGAGGTAAAGGCTGATTTGGTAAAGC |
| 10 | SIP detection probe | GCTCCAGCAGTTCCTGTGACTACGACTTC |
| 11 | SIP detection probe | CGGAAGGTATGACACCAGAAGCAGCA |
| 12 | CFB forward primer | GTGGCTGGTGCATTGTTATTT |
| 13 | CFB reverse primer | CCATTTGCTGGGCTTGATTATT |
| 14 | CFB forward primer | TAGTGGCTGGTGCATTGTT |
| 15 | CFB reverse primer | CATTTGCTGGGCTTGATTATTACT |
| 16 | CFB forward primer | CTGGAATACACGCTTTACTAGAGATA |
| 17 | CFB reverse primer | ACTTGTTGTACCGTAACATTTGG |
| 18 | CFB forward primer | TATCTATCTGGAACTCTAGTGGCT |
| 20 | CFB forward primer | CAAAGATAATGTTCAGGGAACAGA |
| 21 | CFB reverse primer | GCTTCTACACGACTACCAATAGA |
| 22 | CFB detection probe | ACCACTTGTGGAGTTGTCACTTGATCAGC |
| 23 | CFB detection probe | CAAGTGACAACTCCACAAGTGGTAAATCATGT |
| 24 | CFB detection probe | AGCAATCACACATGCTGTTGGAGTTCAGT |
| 25 | CFB detection probe | TTGCGTGCCAACCCTGAGACAGTTTA |
| 26 | CFB oligomer hybridizing region | TATCTATCTGGAACTCTAGTGGCTGGTGCATTGTTATTT |
| 27 | CFB oligomer hybridizing region | TAGTGGCTGGTGCATTGTTATTT |
| 28 | CFB oligomer core sequence | GTGGCTGGTGCATTGTT |

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

What is claimed is:

1. A method for determining the presence or absence of Group B *Streptococcus* (GBS) in a sample, said method comprising:
   (1) contacting a sample containing or suspected of containing GBS with an amplification oligomer combination comprising first and second synthetic surface immunogenic protein (SIP)-specific amplification oligomers for amplifying a target region of a GBS SIP target nucleic acid, wherein the first and second synthetic SIP-specific amplification oligomers are each less than 60 nucleotides in length and comprise, respectively, first (A) and second (B) SIP-specific target-hybridizing sequences selected from the group consisting of:
   (a) (A) SEQ ID NO:3, or an RNA equivalent or DNA/RNA chimeric thereof, and
      (B) SEQ ID NO:4, or an RNA equivalent or DNA/RNA chimeric thereof; and
   (b) (A) SEQ ID NO:7, or an RNA equivalent or DNA/RNA chimeric thereof, and
      (B) SEQ ID NO:8, or an RNA equivalent or DNA/RNA chimeric thereof;
   (2) performing an in vitro nucleic acid amplification reaction, wherein performing the in vitro nucleic acid amplification reaction comprises incubating the sample and the SIP-specific amplification oligomers under conditions suitable for amplification, wherein the target region of the GBS SIP target nucleic, if present in the sample, is amplified to generate an amplicon; and
   (3) contacting the in vitro nucleic acid amplification reaction with a SIP-specific detection probe oligomer comprising a detectable label and a SIP-specific detection probe target-hybridizing sequence that is from about 15 to about 35 nucleotides in length and is configured to hybridize to a target sequence contained within a SIP amplicon amplifiable by the first and second synthetic SIP-specific amplification oligomers, wherein SIP-specific detection probe oligomer provides a detectable signal in the presence of the amplicon;
   wherein the presence of the detectable signal indicates the presence of GBS in the sample and absence of the detectable signal indicates the absence of the GBS in the sample.

2. The method of claim 1, wherein the first and second SIP-specific target-hybridizing sequences are the target-hybridizing sequences of (a).

3. The method of claim 1, wherein the first and second SIP-specific target-hybridizing sequences are the target-hybridizing sequences of (b).

4. The method of claim 1, wherein the first and second SIP-specific target-hybridizing sequences are the target-hybridizing sequences of (a) and the SIP-specific detection probe target-hybridizing sequence is SEQ ID NO:9, or an RNA equivalent or DNA/RNA chimeric thereof.

5. The method of claim 1, wherein the first and second SIP-specific target-hybridizing sequences are the target-hybridizing sequences of (b) and the SIP-specific detection probe target-hybridizing sequence is SEQ ID NO:11, or an RNA equivalent or DNA/RNA chimeric thereof.

6. The method of claim 1, wherein the detectable label is selected from the group consisting of a fluorescent label and a chemiluminescent label.

7. The method of claim 6, wherein the detectable label is a fluorescent label and the detection probe oligomer further comprises a non-fluorescent quencher.

8. The method of claim 1, wherein detectable signal is detected in real time.

\* \* \* \* \*

SEQUENCE LISTING

<160> NUMBER OF SEQ ID NOS: 28

<210> SEQ ID NO 1
<211> LENGTH: 1305
<212> TYPE: DNA
<213> ORGANISM: Artificial Sequence
<220> FEATURE:
<223> OTHER INFORMATION: reference sequence

<400> SEQUENCE: 1

```
atgaaaatga ataaaaaggt actattgaca tcgacaatgg cagcttcgct attatcagtc      60
gcaagtgttc aagcacaaga aacagatacg acgtggacaa cacgtactgt ttcagaggta     120
aaggctgatt tggtaaagca agacaataaa tcatcatata ctgtgaaata tggtgataca     180
ctaagcgtta tttcagaagc aatgtcaatt gatatgaatg tcttagcaaa aattaataac     240
attgcagata tcaatcttat ttatcctgag acaacactga cagtaactta cgatcagaag     300
agtcacactg ccacttcaat gaaaatagaa acaccagcaa caaatgctgc tggtcaaaca     360
acagctactg tggatttgaa aaccaatcaa gtttctgttg cagaccaaaa agtttctctc     420
aatacaattt cggaaggtat gacaccagaa gcagcaccaa cgattgtttc gccaatgaag     480
acatattctt ctgcgccagc tttgaaatca aaagaagtat tagcacaaga gcaagctgtt     540
agtcaagccg cagctaatga acaggtatca ccagctcctg tgaagtcgat tacttcagaa     600
gttccagcag ctaaagagga agttaaacca actcagacgt cagtcagtca gtcaacaaca     660
gtatcaccag cttctgttgc cactgaaaca ccagctctag tagctaaagt agcaccggta     720
agaactgtag cagcccctag agtgacaagt gctaaagtag tcactcctaa agtagaaact     780
ggtgcatcac cagagcatgt atcagctcca gcagttcctg tgactacgac ttcaacagct     840
acagacaata agttacaagc gactgaagtt aagagcgttc cggtagcaca aaaagctcca     900
acagcaacac cggtagcaca accagcttca acaacaaatg cagtagctgc acatcctgaa     960
aatgcagggc tccaacctca tgttgcagct tataaagaaa aagtagcgtc aacttatgga    1020
gttaatgaat tcagtacata ccgtgcggga gatccaggtg atcatggtaa aggtttagca    1080
gttgacttta ttgtaggtac caatcaagca cttggtaatg aagttgcaca gtactctaca    1140
caaaatatgg cagcaaataa catttcatat gttatctggc aacaaaagtt ttactcaaat    1200
acaaatagta tttatggacc tgctaatact tggaatgcaa tgccagatcg tggtggcgtt    1260
actgccaacc actatgacca cgttcacgta tcatttaaca ataa                     1305
```

<210> SEQ ID NO 2
<211> LENGTH: 768
<212> TYPE: DNA
<213> ORGANISM: Artificial Sequence
<220> FEATURE:
<223> OTHER INFORMATION: reference sequence

<400> SEQUENCE: 2

```
atgaacgtta aacatatgat gtatctatct ggaactcgag tggctggtgc attgttattt      60
tcaccagctg tattagaagt acatgctgat caagtgacaa ctccacaagt ggtaaatcaa     120
gtaaatagta ataatcaagc ccagcaaatg gctcaaaagc ttgatcaaga tagcattcag     180
ttgagaaata tcaaagataa tgttcaggga acagattatg aaaaaccggt taatgaggct     240
```

```
attactagcg ttgaaaaatt aaagacttca ttgcgtgcca accctgagac agtttatgat    300
ttgaattcta ttggtagtcg tgtagaagcc ttaacagatg tgattgaagc aatcactttt    360
tcaactcaac atttaacaaa taaggttagt caagcaaata ttgatatggg atttgggata    420
actaagctag ttattcgcat tttagatcca tttgcttcag ttgattcaat taaagctcaa    480
gttaacgatg taaaggcatt agaacaaaag gttttaactt atcctgattt aaaaccaact    540
gatagagcta ccatctacac aaaatcaaaa cttgataagg aaatttggaa tacacgtttt    600
actagagata aaaaagtact taacgtcaaa gaatttaaag tttacaatac tttaaataaa    660
gcaatcacac atgctgttgg agttcagttg aatccaaatg ttacggtaca acaagttgat    720
caagagattg taacattaca agcagcactt caaacagcat taaaataa                768

<210> SEQ ID NO 3
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 3
cagtcgcaag tgttcaagc                                                  19

<210> SEQ ID NO 4
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 4
aacgcttagt gtatcaccat at                                              22

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5
cggtaagaac tgtagcagcc                                                 20

<210> SEQ ID NO 6
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 6
gctcttaact tcagtcgctt g                                               21

<210> SEQ ID NO 7
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 7
aacaaatgct gctggtcaaa                                                 20
```

<210> SEQ ID NO 8
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 8
agaatatgtc ttcattggcg aa                                          22

<210> SEQ ID NO 9
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 9
actgtttcag aggtaaaggc tgatttggta aagc                             34

<210> SEQ ID NO 10
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 10
gctccagcag ttcctgtgac tacgacttc                                   29

<210> SEQ ID NO 11
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 11
cggaaggtat gacaccagaa gcagca                                      26

<210> SEQ ID NO 12
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 12
gtggctggtg cattgttatt t                                           21

<210> SEQ ID NO 13
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 13
ccatttgctg ggcttgatta tt                                          22

<210> SEQ ID NO 14
<211> LENGTH: 19
<212> TYPE: DNA
<213> ORGANISM: Artificial Sequence
<220> FEATURE:
<223> OTHER INFORMATION: synthetic oligonucleotide

```
<400> SEQUENCE: 14
tagtggctgg tgcattgtt                                            19

<210> SEQ ID NO 15
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 15
catttgctgg gcttgattat tact                                      24

<210> SEQ ID NO 16
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 16
ctggaataca cgctttacta gagata                                    26

<210> SEQ ID NO 17
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 17
acttgttgta ccgtaacatt tgg                                       23

<210> SEQ ID NO 18
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 18
tatctatctg gaactctagt ggct                                      24

<210> SEQ ID NO 19

<400> SEQUENCE: 19

000

<210> SEQ ID NO 20
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 20
caaagataat gttcagggaa caga                                      24

<210> SEQ ID NO 21
<211> LENGTH: 23
<212> TYPE: DNA
<213> ORGANISM: Artificial Sequence
<220> FEATURE:
<223> OTHER INFORMATION: synthetic oligonucleotide
```

<400> SEQUENCE: 21
gcttctacac gactaccaat aga        23

<210> SEQ ID NO 22
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 22
accacttgtg gagttgtcac ttgatcagc        29

<210> SEQ ID NO 23
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 23
caagtgacaa ctccacaagt ggtaaatcat gt        32

<210> SEQ ID NO 24
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 24
agcaatcaca catgctgttg gagttcagt        29

<210> SEQ ID NO 25
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 25
ttgcgtgcca accctgagac agttta        26

<210> SEQ ID NO 26
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 26
tatctatctg gaactctagt ggctggtgca ttgttattt        39

<210> SEQ ID NO 27
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 27
tagtggctgg tgcattgtta ttt        23

<210> SEQ ID NO 28

```
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 28
gtggctggtg cattgtt                                                    17
```